(12) United States Patent
Alizadeh et al.

(10) Patent No.: US 10,234,378 B2
(45) Date of Patent: Mar. 19, 2019

(54) METHOD AND SYSTEM FOR REDUCTION OF INFLUENCE OF BASELINE DISTORTION IN ABSORPTION SPECTROSCOPY MEASUREMENTS

(71) Applicant: Servomex Group Limited, East Sussex (GB)

(72) Inventors: Bahram Alizadeh, East Sussex (GB); James Hobby, East Sussex (GB); Martin Lopez, East Sussex (GB); Ian Gaskin, East Sussex (GB)

(73) Assignee: Servomex Group Limited, East Sussex (GB)

( * ) Notice: Subject to any disclaimer, the term of this patent is extended or adjusted under 35 U.S.C. 154(b) by 0 days.

(21) Appl. No.: 15/355,058

(22) Filed: Nov. 18, 2016

(65) Prior Publication Data

US 2017/0138846 A1 May 18, 2017

(30) Foreign Application Priority Data

Nov. 18, 2015 (GB) .................................. 1520357.3

(51) Int. Cl.
*G01N 21/3504* (2014.01)
*G01N 21/27* (2006.01)
*G01N 21/39* (2006.01)
*G01J 3/28* (2006.01)
*G01J 3/433* (2006.01)

(52) U.S. Cl.
CPC ............ *G01N 21/3504* (2013.01); *G01J 3/28* (2013.01); *G01J 3/4338* (2013.01); *G01N 21/274* (2013.01); *G01N 21/39* (2013.01); *G01J 2003/4334* (2013.01); *G01N 2021/399* (2013.01); *G01N 2201/126* (2013.01); *G01N 2201/127* (2013.01)

(58) Field of Classification Search
CPC ......... G01N 2021/399; G01N 21/3504; G01N 21/39; G01N 2201/126; G01N 2201/127; G01N 21/274; G01J 2003/423; G01J 3/42; G01J 3/433
USPC .................................................. 356/432–448
See application file for complete search history.

(56) References Cited

U.S. PATENT DOCUMENTS

2005/0231718 A1* 10/2005 Goodall ............. G01N 21/0303
356/344

FOREIGN PATENT DOCUMENTS

| EP | 2985592 A1 | 2/2016 |
|---|---|---|
| GB | 2524725 A | 10/2015 |
| WO | 2013096396 A1 | 6/2013 |

OTHER PUBLICATIONS

Foreign Correspondence From a Related Counterpart Application, GB Combined Search and Exam Report dated Jan. 11, 2016, GB Application No. 1520357.3.
(Continued)

*Primary Examiner* — Tri T Ton

(57) ABSTRACT

A method and system for reducing the effect of distortions on the baseline signal in an absorption spectroscopy system used for the detection or measurement of chemical species in a medium, whereby one or more correlations or convolutions are performed on the signal using a kernel function. The shape of the kernel function is chosen to reduce the influence of the baseline distortions on the processed measurand determination. The kernel function may also be chosen to enhance the absorption signal.

30 Claims, 18 Drawing Sheets

(56) References Cited

OTHER PUBLICATIONS

Foreign Correspondence From a Related Counterpart Application, EP Extended Search Report dated Apr. 13, 2017, EP Application No. 16199293.8.
Rieker G B et al: "Calibration-free wavelenght-modulation spectroscopy for measurements of gas temperature and concentration in harsh environments". Applied Optics. Optical Society of America. Washington. DC; US. vo 1 • 48. No. 29. Oct. 5, 2009 (Oct. 5, 2009). pp. 5546-5560. XP001549203. ISSN: 0003-6935. DOI: 10.1364/A0.48.005546.
May R D et al: "Data processing and calibration for tunable diode laser harmonic absorption spectrometers". Journal of Quantitative Spectroscopy and Radiative Transfer. Elsevier Science. Oxford. GB. vol. 49. No. 4. Apr. 1993 (Apr. 1993). pp. 335-347. XP024434779. ISSN: 0022-4073. DOI: 10.1016/0022-4073 (93)90098-3.
Wheaetley, Brad, "Tunable Diode Laser Absorption Spectroscopy of Hypersonic Flows", ICAS 2012 28th International Congress of the Aeronautical Sciences, 2012, XP055353471.

\* cited by examiner

METHOD AND SYSTEM FOR REDUCTION OF INFLUENCE OF BASELINE DISTORTION IN ABSORPTION SPECTROSCOPY MEASUREMENTS

CROSS-REFERENCE TO RELATED APPLICATIONS

This application claims priority to United Kingdom Application No. 1520357.3 filed with the Intellectual Property Office of the United Kingdom on Nov. 18, 2015 and entitled, Method and system for reduction of influence of baseline distortion in absorption spectroscopy measurements", which is incorporated herein by reference in its entirety for all purposes.

FIELD OF THE INVENTION

This invention relates to absorption spectroscopy in general and to tunable diode laser absorption spectroscopy in particular. The invention has applications in, among other things, the detection and measurement of one or more species in a gas produced by an artificial or natural process such as an industrial, medical or physiological process.

BACKGROUND

Tunable laser wavelength modulation absorption spectroscopy is finding widespread use in various applications. One such application is the quantification of the amount of chemical species (the measurand) in a substance and in particular in an artificial or natural process such as an industrial, medical or physiological process gas analysis where an improved performance may be obtained compared to other techniques.

A typical system consists of a tunable laser source such as a tunable diode laser (TDL) that emits a beam of light that is focussed on a detector. The substance that is to be analysed is positioned between the tunable laser source and the detector, so that the light incident on the detector has been modified by its passage through the substance. The modifications to the light enable various parameters of the measurand to be determined by a signal processing system that is coupled to the detector. In some cases the substance to be analysed is a gas produced by an industrial process, and the measurand may be one or more chemical species that are present in this process gas. Examples of measurand species include but are not limited to gaseous water, $O_2$, CO and $CO_2$ and hydrocarbons such as methane. The presence and/or amount fraction (concentration) of one or more of these measurand species may be determined by absorption spectroscopy measurements using one or more TDLs.

In operation of the laser gas analyser system, the wavelength of the beam emitted by the TDL is scanned over a range of wavelengths including one or more absorption lines of the measurand. At certain specific wavelengths within the range of wavelengths scanned, light is absorbed by the measurand and these spectral absorption lines can be detected by measuring the light transmitted through the substance to be analysed. This allows the necessary spectroscopic information to be acquired to determine not only the amount fraction of the measurand, but also optionally to determine the influence of pressure, temperature or background mixture composition. In some cases it is possible to use a single laser source to measure a plurality of measurands. In these cases, the output wavelength of the laser source is swept across a wavelength range that includes at least one discernable absorption line for each of the plurality of measurands.

In a well-designed system, wavelength modulation techniques offer very high sensitivity and enhanced spectral resolution. In particular, second harmonic wavelength modulation spectroscopy is well suited to gas analysis due to its ability to cope with a wide variety of spectroscopic situations found in industrial processes, such as congested absorption spectra, sensitive trace level measurements and obscured optical transmission.

This is shown by the folloing relationships, where equation [1] represents the Beer-Lambert law of optical absorption, wherein u is the molecular density per unit length of the measurand, I is the detected amount of light, $I_0$ is the incident amount of light (equal to unabsorbed amount when the molecular density is zero), v is the frequency of light and "a" is the absorption coefficient.

$$\log\left[\frac{I(v)}{I_0(v)}\right] = -u.a(v) \quad [1]$$

The change in the amount of light detected at any particular frequency ($\partial I(v)$) is related to the molecular density change ($\partial u$) by differentiating equation [1] and is given by equation [2].

$$\partial u = \frac{\partial I_0(v)}{a(v)I_0(v)} - \frac{\partial I(v)}{a(v)I(v)} \quad [2]$$

Equation [2] shows that if other ambient conditions are stable or corrected for, the change in detected intensity will be proportional to the change in molecular density ($\partial u$), but the detected intensity is also affected by any variations in the amount of incident light ($\partial I_0(v)$)

Variations in incident amount of light may be caused by a number of factors other than absorbing molecular density changes. For example, variations can be caused by intrinsic fluctuations in the laser output, changes in ambient light intensity levels and/or obscuration in the process sample stream, which may be caused by any combination of dust, tar, corrosion or optical beam misalignment. Obscuration and changing of the intensity of ambient light are to be expected in a furnace. If the variation in incident light is not corrected, this will result in a measurement uncertainty (error) in the processed measurand concentration. Techniques have been developed to deal with these sources of uncertainty, such as described in published patent application GB2524725 (Kovacich et al), which is incorporated herein by reference.

However, there is another potential cause of fluctuations in the optical detector signal, which is not due to direct fluctuations in the ambient light or laser output signal, but due to constructive and destructive interference occurring and causing an oscillation in the detector signal as the laser is scanned across the measurement wavelength range. The use of coherent laser light means that any reflections at any optical surfaces or interfaces along the optical path from the laser output to the detector surface (for example from surfaces/interfaces such as, windows, lenses and reflective interfaces), lead to the production of reflected light with a phase difference in comparison with the incident light, hence leading to optical interference where the light rays interact. The phase relationship between this reflected light and the incident light may change with time due to such factors as temperature, vibration and pressure fluctuations, since these factors may cause physical dimensional, density or refractive index changes.

The detector is integrating this optical interference to produce an intensity signal. Since the phase difference will vary with wavelength along the measure path, the symptoms of this optical interference (or etalons) are typically the production of oscillations on the signal baseline as the laser output is scanned across the wavelength measurement range. These combine with other distortions and cause measurement inaccuracies. The signal "baseline" is the signal that would be seen even if no absorbing signal were present, in other words, the "zero absorption" signal. This baseline signal is superimposed on the actual absorption signal when present. In an ideal world, the baseline would be a straight line (flat line centred at zero in perfect circumstances), but in practice this is never achieved. The baseline may not be perfectly flat across the scan range and may have fluctuations and other distortions (or "noise"), which may be of a random or systematic nature and include the above-mentioned oscillations. These oscillations are also known as "fringe" signals in the case of optical interference. These various distortion effects, of whatever origin, lead to increased uncertainty in the determination of the absorption signal or signals, and hence increased uncertainty in the derived molecular density or concentration of the measurand.

One method to decrease such optical interference is to reduce or eliminate any reflective or partially reflective surfaces in the light path from source to detector that may form etalons, such as by minimising the number of optical components, using wedge windows rather than parallel face windows or anti-reflection coating optimised for the desired wavelength range. However, it is impossible in practice to completely eliminate this interference effect by reducing reflective surfaces. In cases where a multipass cell is used it is unavoidable as the beam path within a multipass cell will always create some amount of optical interference, which is usually significant for trace level measurements.

Another method to reduce the impact of optical interference on the baseline is to measure and record a reference baseline when no measurand is present. This reference baseline may then be subtracted from the live signal to produce a cleaner signal to process. Whilst this may give an immediate improvement to the measurand determination uncertainty, it does not address oscillations on the baseline under changes in ambient conditions (particularly temperature) and hence the effectiveness of this technique is limited.

Another method involves the use of a piezo electric element or similar to oscillate an active optical element such as a lens or mirror in the optical path. This has the effect of continuously varying the optical pathlengths and hence the phase variations and resultant optical interference. This results in blurring or smoothing down the sinusoidal oscillation on the baseline, through integration over time of the interference fringes formed and therefore reducing the overall effect. However, it adds complexity, cost, suffers from a number of problems due to using a moving element, such as reduced component lifetime and mechanical failure and, in practice, does not eliminate the problem completely. Moreover, most piezo electric elements require a sufficiently high voltage supply that makes operation in flammable hazardous areas unsuitable.

In addition, there are other potential causes of fluctuations in the baseline signal. These may be optical, such as due to ambient light generation or scattered light, or non-optical, such as caused by electromagnetic interference or random or systematic noise. Electromagnetic interference may be short term or persistent.

Hence, there remains a need for an absorption spectroscopy gas analyser system that can produce highly accurate measurements, despite fluctuations in the baseline signal due to optical interference or other effects, which are changing with time. There is also a need for such an analyser system that is able to produce highly accurate measurements in a harsh environment as may typically be found in many industrial processes, such as in a furnace or furnace exhaust pipe.

Note that although the detailed explanations and systems that follow illustrate use of the invention for second harmonic (2f) wavelength modulation spectroscopy for detection and measurement, the novel technique described in this patent specification is applicable to any harmonic absorption measurement, i.e anything from $1^{st}$ harmonic (direct absorption) to second or higher order harmonics.

SUMMARY

In a first aspect of the invention, there is provided a method for reducing the effects of distortions on the baseline of an absorption signal within an absorption spectroscopy system, comprising the steps of:

controlling a source of electromagnetic radiation to emit a wavelength modulated beam of electromagnetic radiation;

detecting the modulated beam or beams after transmission through a test medium;

processing the detected beam or beams to obtain a signal indicative of the absorption effects of one or more measurands, wherein the processing includes correlating or convolving the indicative signal with a kernel function that is selective for a predicted signal distortion effect.

Correlating or convolving the indicative signal with a kernel function that is selective for a predicted signal distortion effect can mitigate the effects of fluctuations and other distortions on the absorption signal baseline, to reduce uncertainty in the determination of the measurand(s). Despite various uncertainties and variations, the inventors of the present invention have determined that certain features or components of an absorption signal, including signal distortions due to optical interference effects, can be predicted and therefore identified and corrected for. Predicted absorption lines can be emphasized and the effects of distortions can be reduced. For example, optical interference effects resulting from out-of phase reflections (in particular, phase differences that vary with wavelength along the measure path) can be predicted to appear as sinusoidal oscillations on the signal baseline (or "pseudo-sinusoidal" oscillations, which refers herein to a modified sinusoid—a sinusoidal signal with extra components), as the laser output is scanned across the wavelength measurement range.

A second aspect of the invention provides an absorption spectroscopy system, comprising:

a source of electromagnetic radiation for emitting a wavelength modulated photon beam;

a detector for detecting the modulated photon beam or beams after transmission through a test medium;

a signal processing unit for processing the detected beam or beams to obtain a signal indicative of the absorption effects of one or more measurands, wherein the processing unit is adapted to perform processing including correlating or convolving the indicative signal with a kernel function that is selective for a predicted signal distortion effect, for reducing the effect of signal distortions on a measurement of absorption effects of the one or more measurands.

Various embodiments of the invention are described below. In general, the features of these embodiments are complementary and so may be combined or replaced with features of other embodiments, within the scope of the invention.

In some embodiments of the invention, a first kernel function is selected (chosen or generated) to have a profile that emphasizes or suppresses an expected baseline distortion profile. In many systems, this would be considered impossible because distortions such as optical and electromagnetic interference effects and other "noise" are considered to be random or at least unpredictable effects. The inventors of the present invention have recognized that some components of signal "noise" are identifiable by prediction of the characteristic profile of the noise component, and can be corrected for by convolving or correlating with a kernel that is selective for a predicted signal distortion effect, to emphasize or diminish certain predicted distortions of the signal. This prediction of the presence of certain signal distortion effects and processing of the absorption signal using one or more kernel functions, leads to more accurate measurements. A number of kernel functions can be used that are each optimal for a predicted feature or component of the signal.

In an embodiment, a baseline kernel or inverse baseline kernel may be correlated or convolved with the signal to determine the "corrected" baseline signal and hence used to reduce the effect of the predictable shape aspects of baseline distortion. This reference to a corrected baseline signal is intended to refer to the processed baseline signal which represents what would be seen if the influence of systematic noise were reduced or eliminated.

In some embodiments, a kernel function is selected to have a profile corresponding to or selective for a predicted absorption signal profile. This can be used to enhance the absorption signal, by removing or reducing the effects of "noise" on the measured signal. The kernel may be correlated or convolved with the signal to reduce the effect of the shape aspects of the baseline distortion.

In some embodiments of the invention, a first kernel function is selected to identify predictable signal fluctuations and other distortions, to remove them or reduce their effect, and then a second kernel function is selected and used to further enhance the absorption signal.

In other embodiments, a single kernel may be correlated or convolved with the signal both to reduce the effect of the shape aspects of the fluctuations on the baseline and to enhance the shape aspects due the absorption signal and hence reduce the relative effect of optical interference on the baseline.

In some embodiments, the absorption shape profile is derived from a measured known reference spectrum.

In some embodiments, the correlation or convolution of kernel and signal is processed in the time domain.

In some embodiments, the correlation or convolution of kernel and signal is processed in the frequency or Fourier domain.

In some embodiments, the kernel used in the correlation or convolution may be comprised of a Lorentzian, Gaussian or Voigt, to emphasize desired signal features, or a sinuisoidal function to identify and reduce or emphasize sinusoidal fluctuations on the baseline signal, or a combination of two or more of these functions.

In some embodiments, the kernel used in the correlation or convolution may be derived from an empirical shape, a theoretical shape or a combination of both.

In some embodiments, the signal may be derived by second harmonic (2f) wavelength modulation spectroscopy or other harmonic detection and may involve a compensation technique for light intensity fluctuations such as a 2f or other frequency modulation burst that can be used as a reference signal.

In some embodiments, a kernel may be correlated or convolved with the signal to reduce the effect of the shape aspects of the fluctuations on the baseline and to enhance the shape aspects due to a modulation burst that is used as a reference signal, and hence reduce the relative effect of baseline distortions on the light intensity compensation.

In some embodiments, a kernel may be correlated or convolved with the signal to reduce the effect of the shape aspects of the fluctuations on the baseline and to enhance the shape aspects due a reference modulation burst and absorption signals, and hence reduce the relative effect on measurement accuracy of fluctuations on the baseline.

The optimal kernel shape can vary according to the gas to be measured and the ambient conditions such as background gas, temperature and pressure. In some instances, the preferred kernel to be used for a specific measurand will change in accordance with ambient conditions, and so the invention may be implemented to switch between kernel function, for example using a Lorentzian kernel for low temperature, high pressure ambient conditions and using a Gaussian kernel for high temperature, low pressure conditions and using a Voigt kernel for the intermediate zone.

In some specific instances, the kernel shape may correspond to a compound absorption line, such as a doublet or triplet or higher order.

The kernel shape may also be derived empirically, theoretically or a combination of both.

Additionally, the kernel may be sinusoidal, pseudo-sinusoidal or any other defined shape that corresponds or is related to the shape or inverse shape of the baseline distortion pattern on the baseline, and may be derived theoretically, empirically or through a combination of both.

The kernel may also be a combination of two or more of the shape functions described above.

In some embodiments, the kernel uses a live or stored signal from an internal reference cell. The internal reference cell may be an optical element and/or may contain the measurand or measurands to be determined in the sample and/or may contain another absorbing compound (or other compounds) which absorbs (absorb) in a region close to the measurand absorption feature to be measured, which has (have) a defined relationship with the measand feature to be measured. The defined relationship may be the relative position of the reference absorption line in comparison to the absorption line of interest of the measurand and/or may be the line shape of the reference is similar to the line shape of the measurand to be determined. The internal reference cell may also be temperature controlled and/or have a temperature sensor and/or pressure controlled and/or have a pressure sensor. The internal reference signal may be derived by directing a portion of the laser light used to obtain the primary absorption signal (i.e. the measurand) into a secondary absorption light path via an optical element such as a beam splitter or partially reflective element. This secondary absorption line path may then be directed through a reference cell (such as an optically transmissive cuvette containing the reference mixture—sealed or flushable with reference mixture) onto a secondary optical detector. This reference signal from the internal reference cell is therefore obtained under known conditions. The present invention may be used to mitigate the effects of signal distortions on the internal reference cell signal, the method then including processing the signal obtained using the internal reference cell by convolving or correlating with a suitable kernel function.

In an alternative embodiment, the internal reference cell is used to provide a signal indicative of absorption by one or more measurands, which is then used to generate a kernel function for processing a signal detected after transmission of a wavelength modulated beam through a test medium.

An embodiment where the kernel includes multiple absorption lines of the measurand.

The selected kernels can have defined properties such as net area or aspect ratio.

The method is advantageous for measurement of the amount fraction of one or more measurand species in a gas containing volume, for an artificial or natural process, such as for medical, physiological or industrial process gas analysis. This measurement could be in situ such as across a furnace or the exhaust pipe of a furnace or other industrial process chamber or gas cell, or it could take place in an extractive system, for example including gas conditioning means such as involving temperature control and/or dehumidification. The measurement could involve a single light beam pass measurement or a multi-pass measurement using a retro-reflector or other suitable means such as a White or Heriott cell arrangement to extend the effective light path within a confined length. Such arrangements for extending the light path are known to those skilled in the art and will not be discussed further here.

The method of correcting is particularly beneficial for tunable diode laser absorption spectroscopy (TDLS), where the diode laser can be controlled by applying a modulated control signal to the diode laser's bias current. The inventors of the present invention have determined that application of a correlation or convolution technique with a defined kernel function can reduce the influence of unwanted baseline oscillations.

BRIEF DESCRIPTION OF THE DRAWINGS

Embodiments of the present invention are described below, by way of example only, with reference to the following drawings in which:

FIG. 13(*b*) shows the signal for a TDLS second harmonic system with zero padding applied.

DETAILED DESCRIPTION OF EMBODIMENTS

Figure 1:
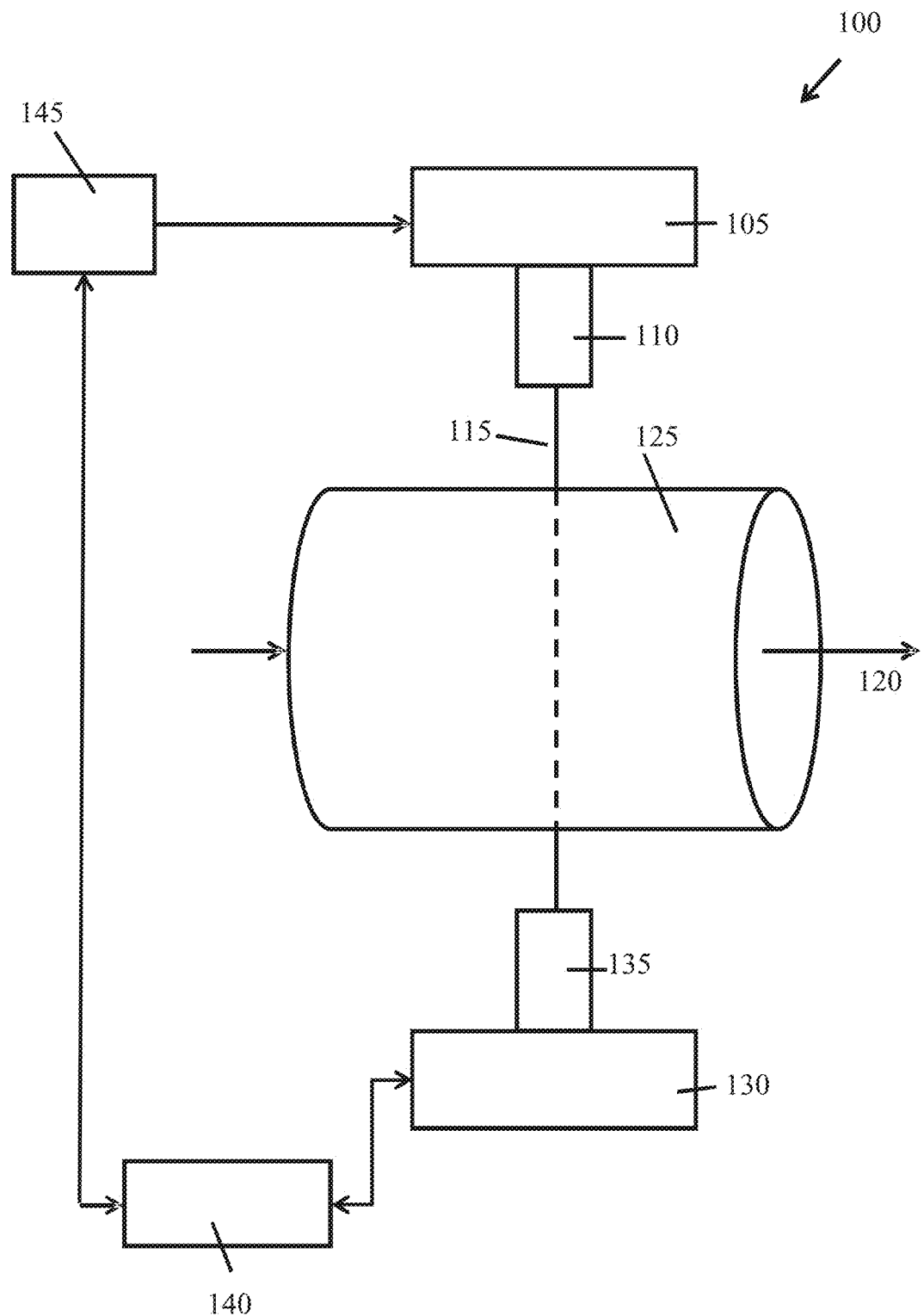
FIG. 1 is a schematic diagram of a laser gas analyser system deployed as an industrial process gas analyser.

Embodiments of the invention are best understood in the context of the broader system in which they operate. FIG. 1 shows, in schematic form, the major components of a typical laser gas analyser system 100. System 100 includes a laser 105, which may be a tunable laser such as a tunable diode laser (TDL). Tunable diode lasers are well known to the skilled person and so will not be described in further detail here.

Optionally, a laser mount 110 may be provided to secure laser 105 in position. If present, preferably laser mount 110 allows fine adjustment to the angle of laser 105 to facilitate beam alignment. Laser mount 110 may include a window (not shown) that is transparent to at least the wavelengths of light emitted by laser 105.

Laser 105 emits a beam 115 of a specific wavelength λ. Where laser 105 is a tunable laser, λ can be varied by a controller 145 of the laser 105 using methods known to those skilled in the art. For example, in the case of a TDL, λ can be varied by adjusting one or both of the temperature of the laser and the diode bias current. Typically the bias current is varied so as to cause λ to vary as a function of time in a manner that causes it to sweep across one or more absorption lines corresponding to the measurand species that the system is to detect. Sweep frequencies in the range of hertz to kilohertz may be achieved. λ may be in the near-infrared portion of the electromagnetic spectrum. λ may be in the range of about 200 nm to about 16000 nm. λ will be chosen by the skilled person depending on the measurand species and the need for the wavelength range of the TDL to encompass one or more absorption peaks of the measurand species.

Beam 115 is directed such that it passes through a volume containing a sample that is to be analysed. In the embodiment of FIG. 1, the sample is a gas mixture 120 that is produced in or flowing through a chamber 125, but it will be appreciated that variations to this arrangement will be made according to the environment that system 100 is deployed in. Chamber 125 may be a furnace or a pipe such as a furnace exhaust pipe or a gas cell. Gas mixture 120 may be the gases produced by an industrial process, such as furnace exhaust gases, or gases used in artificial or natural process applications. A window (not shown) may be provided in chamber 125, to allow beam 115 to penetrate chamber 125 and pass through gas mixture 120. Another window (not shown) may be provided in chamber 125 to allow beam 115 to exit chamber 125.

System 100 also includes a detector 130 that is capable of detecting light at the wavelengths emitted by laser 105. Detector 130 may be a photodetector of any type known to the skilled person, e.g. a photo diode. Optionally, a detector mount 135 may be provided to secure detector 130 in position. If present, preferably detector mount 135 allows fine adjustment to the angle of detector 130 to facilitate alignment with the transmitted beam. Detector mount 130 may include a window (not shown) that is transparent to at least the wavelengths of light emitted by laser 105. One or more interference filters (not shown) may be provided in front of detector 130, possibly as part of detector mount 135, to substantially reduce the intensity of ambient light falling on detector 130. In some embodiments additional opto-mechanical segments are present to purge the dead volumes in the absorption pathlength and/or to maintain optical features such as lenses or windows clean and scratch free and/or to manage the surface temperatures.

Gas mixture 120 may include a number of different components. These may be one or more elements, compounds, or a mixture of elements and compounds. Typical components include but are not limited to any combination of $O_2$, CO, $CO_2$, gaseous $H_2O$ and hydrocarbons such as $CH_4$. System 100 may operate to detect the presence of one or more of the components of gas mixture 120. The components to be detected will be referred to hereafter as 'measurands'. System 100 may operate to additionally or alternatively determine at least one parameter of the one or more measurands, such as the amount fraction. The determined at least one parameter may be used as an input for controlling an industrial process, possibly as feedback for a feedback loop. Each measurand has one or more absorption lines in their absorption spectrum. Absorption lines are well known to the skilled person and will not be described further here.

Detector 130 and laser 105 are communicatively coupled to an electronic detection system 140. The couplings are depicted as double headed arrows in FIG. 1. Electronic detection system 140 may be a printed circuit board (PCB) including at least one processor and a memory. Electronic detection system 140 may additionally include any combination of second harmonic detection electronics, a demodulation filter and a demodulation mixer or switch. Electronic detection system (140) may also include digital electronics to allow digital signal manipulation and processing techniques and to provide user interfaces, although analogue techniques are also possible. One skilled in the art will realise that modifications to this arrangement according to the particulars of a given system are possible.

A controller 145 is configured to control laser 105, including controlling the laser output wavelength λ. In the case where laser 105 is a TDL, the controller 145 is configured to adjust at least the diode laser bias current as a function of time and may also include temperature control of the diode laser. Further details of this adjustment are given later in this specification.

Electronic detection system 140 is also configured to receive an output signal from detector 130 that is indicative of the light incident on detector 130 as a function of time. Electronic detection system 140 is further configured to process this output signal, as described in more detail later in this specification. Electronic detection system 140 may be configured to be coupled to a display device (not shown) and may be configured to allow the display device to show one or more of the raw output from detector 130, a processed output from detector 130, a wavelength of laser 105 and a laser bias current. Other parameters may be shown in place of or in addition to any combination of these parameters. One skilled in the art will be able to construct electronic detection system 140 according to these specifications without difficulty.

Figure 2:
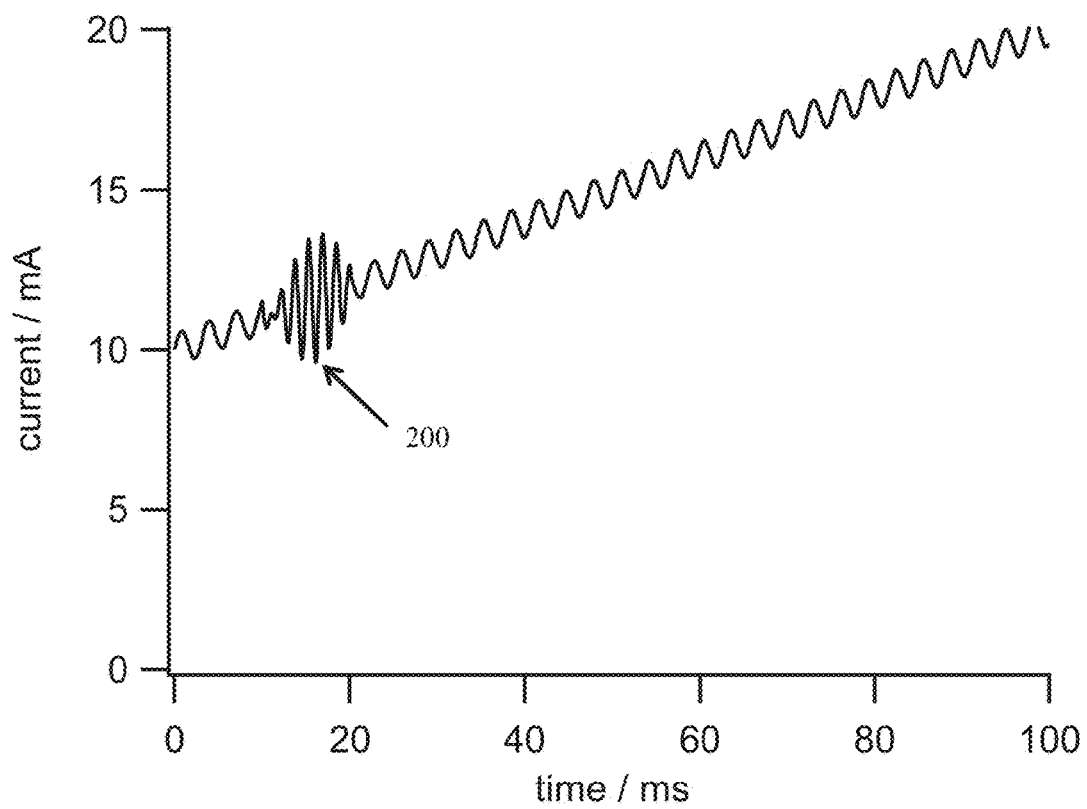
FIG. 2 is a plot showing, as a function of time, a bias current applied to a diode laser forming part of a tunable diode laser.

FIG. 2 shows, as a function of time, the bias current applied to a diode laser forming part of a tunable diode laser. The bias current is generated by the controller 145. As can be seen from FIG. 2, the bias current includes three components. The first is a low frequency ramp (linear in this illustration) to scan the TDL output wavelength at a constant rate over one or more absorption lines of the measurand, or one or more absorption lines of each of a set of measurands.

In addition to this low frequency scan, in some embodiments a second much higher frequency bias current modulation (e.g. sinusoidal modulation) can be added. This high frequency bias current modulation is optional, and is provided to allow wavelength modulation spectroscopy to be performed (e.g. second harmonic detection).

Wavelength modulation spectroscopy is advantageously used when the laser spectroscopy is performed in a congested part of the electromagnetic spectrum; i.e. where there are many absorption lines close to one another, or even overlapping absorption lines. This is because it provides enhanced resolution that may be necessary to pick out a specific absorption line of the measurand among interfering absorption lines due to other chemical species from the background mixture. In some cases second harmonic wavelength modulation spectroscopy is preferable over direct absorption or first harmonic wavelength modulation spectroscopy because the second harmonic technique affords a greater resolution. The electronic techniques for performing first and second harmonic laser wavelength modulation spectroscopy are well established and known by those skilled in the art.

In the case of second harmonic wavelength modulation spectroscopy, in one particular embodiment electronic detection system 140 is configured to select the second harmonic signal that is generated by the effect of the absorption line on the frequency modulated laser signal, which is then converted to a photo-current signal at twice the modulation frequency by the photo-diode (or other suitable light sensitive element) that receives the incident light. As the second harmonic signal is detected in a very narrow spectral pass band, the noise rejection is extremely high, allowing highly sensitive chemical species detection. The process is similar for other harmonic detection schemes, such as first and third harmonics, but the signals become progressively weaker as the harmonic order increases and the second harmonic signal offers the best balance between signal strength, noise rejection and spectral resolution.

A third component of the bias current may be present, which is an artificially generated second harmonic signal (i.e. at twice the frequency of the applied second component modulation) of typically short duration, herein referred to as the second harmonic burst 200. The burst duration should ideally exceed the settling time of the demodulation filter, as this helps with reliable measurement. This second harmonic burst 200 is applied to provide a controlled reference signal for correction of fluctuations in incident light. From a signal processing perspective, this is optimally achieved by a third component of the bias current. Other light intensity corrective means are possible and known to those skilled in the art and will not be discussed further here.

An illustration of the three components of the bias current is shown below:

Bias current=Ramp Function+High Frequency Modulation+Burst Signal

The second harmonic burst 200 is applied to the tunable diode laser's bias current to provide a controlled reference signal for correction of fluctuations in incident light caused by, for example, variations in the laser power or ambient light fluctuations. In the exemplary embodiment of FIG. 2, second harmonic burst 200 begins at about 10 ms and ends at around 20 ms, but the second harmonic burst can be applied at other times during the bias current sweep. The timing and duration of the second harmonic burst is preferably chosen so that it does not overlap at all with the time window in which the output wavelength of the diode laser is tuned to an absorption line of the measurand.

In some embodiments the detected second harmonic burst signal advantageously passes directly into second harmonic detection electronics that are part of electronic detection system 140. This means that no additional signal processing electronics are required to enable processing of the burst signal, which simplifies the overall detection system.

In some embodiments, an alternative approach that achieves a similar effect is adopted. In these embodiments a burst signal is generated at a different, non-interfering frequency from the absorption modulation frequency and a separate signal processing means is used to detect this frequency component. This is less efficient than some embodiments, since it requires additional processing, but this second processing means would provide information pertaining to the laser light intensity, which could then be used in a correcting algorithm.

In many applications, the spectral region of interest may be very congested with background absorption lines and it may be difficult to find a perfectly "neutral" (zero absorption) wavelength zone (region or range). In addition, it may not be possible to eliminate all of the optical interference effects, which will also be affected by mechanical vibration and temperature. Like the absorption signal, the effect of this optical interference may also be mitigated by convolution of the signal with an appropriate kernel function. In addition, one or more of the following techniques for the burst signal may be employed in order to increase the system immunity to these effects. The following techniques involve at least one of these parameters: shape (smoothness), width (duration), amplitude or intensity (peak or dip height), location (both within the scan and as an absolute wavelength range), number of burst signals within a scan, and polarity (phase) of the second harmonic burst signal. These parameters will define the burst signal. The optimum choice of these parameters will vary between applications, laser sources and detection electronics and can be determined by calibration or calculation. The selection criteria and implementation of the optimum 2f burst(s) are described in detail in the published patent application GB2524725 (Kovacich et al.).

For example, the choice of wavelength selected for absorption measurements will depend on the location and strength of the absorption lines of the component of interest, the required amount fraction to be measured for a given path length and the availability and cost of commercial diode lasers. It is also desirable to have an absorption line which is relatively free of background interference. The absorption profile (lines) for a particular component may be measured in the laboratory using suitable equipment or obtained from pre-existing, privately or publicly available, databases such as HITRAN. It is a relatively straight forward task for someone skilled in the art to select an appropriate absorption line taking these considerations into account. Once the absorption line has been selected, the location and duration of the burst signal can then be considered depending on the best "neutral" zone (free from background interference) of the nearby absorption spectrum. This will determine whether the burst signal is best located in front or behind the absorption feature during a scan, or whether it needs to be considered as a separate scan due to the localised congestion of the absorption spectrum around the absorption of the component of interest. For a difficult or congested spectrum, the number and/or polarity of the burst signal(s) can be chosen so as to optimise its application for intensity correction (i.e. in order to distinguish the burst signal from background absorption features). This is especially useful if the background absorption features may change with changing process conditions being measured.

Figure 3:
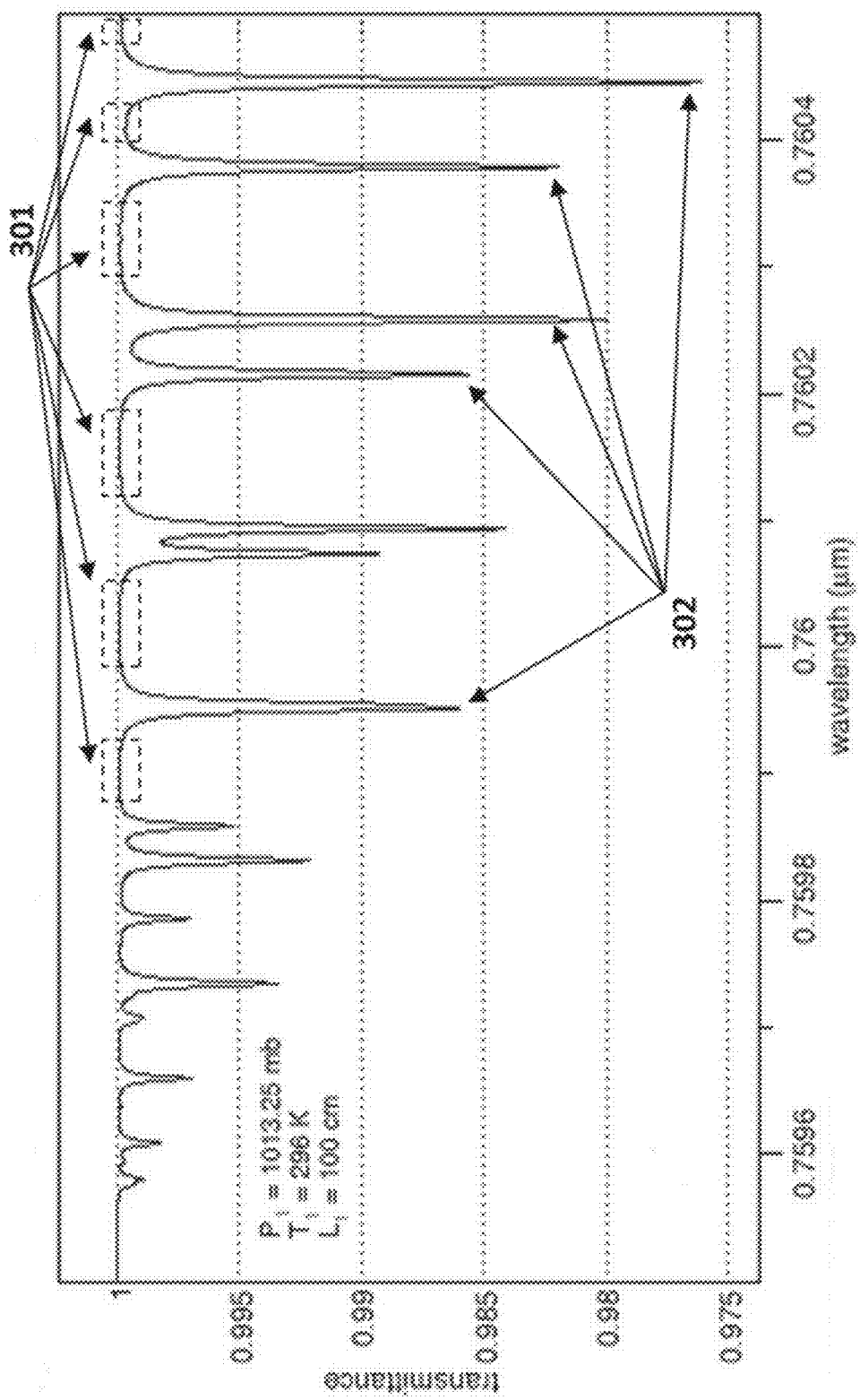
FIG. 3 is a plot showing an absorption profile of oxygen as a function of wavelength.
Figure 4:
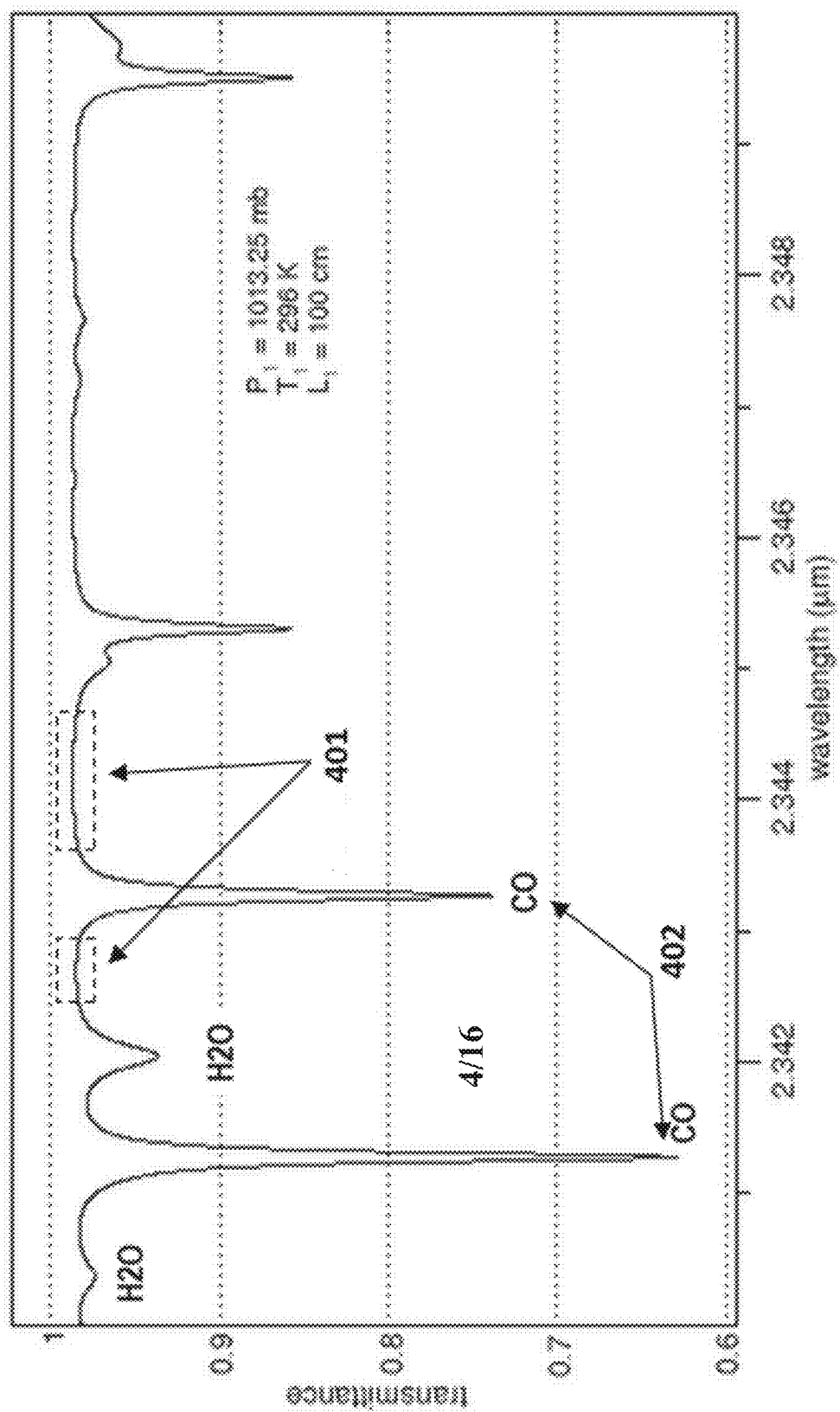
FIG. 4 is a plot showing an absorption profile of carbon monoxide and water as a function of wavelength.

The processes for selecting an appropriate measurement absorption line for a particular measurand and a "neutral" zone for an application are illustrated below for the case of a furnace application measuring oxygen and carbon monoxide using two separate diode lasers. Examples of some absorption lines for these spectra are illustrated using spectra obtained from the HITRAN 2008 database in FIG. 3 for 20% oxygen and FIG. 4 for 2% carbon monoxide and 0.7% water (multiplied one hundred times for illustration). The main gas products when a hydrocarbon fuel is burnt in air are carbon dioxide and water. Carbon monoxide may also be produced by incomplete combustion of the fuel. Under lean (low) oxygen conditions, more carbon monoxide is produced. Therefore, the measurement of carbon monoxide may be used for determining that incomplete combustion is taking place. The results of this incomplete combustion are increased fuel costs due to low furnace efficiency and increased emitted pollution. Conversely, under oxygen rich (high background oxygen) conditions, very low carbon monoxide may be present, but the furnace is still working inefficiently and will require greater fuel usage for the same net heat output since excess air is being heated by the combustion process without providing any extra fuel burn. Therefore, by measuring the amount fractions of oxygen and carbon monoxide, the furnace efficiency may be optimised and pollution minimised through manual or automatic feedback systems to adjust the fuel and/or air levels. The background interference of water lines on the oxygen spectra is low (FIG. 3), whilst that of water on the carbon monoxide spectra is much more significant (FIG. 4). The impact of the background spectra on the measurand is determined both by the relative intrinsic absorption line strengths and the amount fractions of the measurand and the background interferent species. In this application, the amount fraction carbon monoxide levels may be low, whilst the water levels may be much higher. This means that water cross interference should be taken into consideration for carbon monoxide measurements. For a particular path length (100 cm for these illustrations), it is desirable that the absorption strength of the measurand line should be strong enough to give good sensitivity for the measurement and that the absorption line be separate or "clean" i.e. free from any potential interfering line. The interfering line may even be due to the measurand species itself, such as a doublet or triplet formation. Once an appropriate line has been selected, then a nearby "neutral" zone may be selected for locating the burst signal. Several potential absorption lines (302 and 402) and "neutral" zones (301 and 401) are suggested in FIGS. 3 and 4, and any may be chosen since the choice of line will be dependent on application and instrumentation. Note that these illustrations are for room temperature and atmospheric pressure, but equivalent spectra may be obtained for particular furnace measurement conditions. Note also that this example has shown several potential "neutral" zones. In some applications, no perfect "neutral" zone is available and so a compromise zone in terms of location relative to the absorption feature of interest and low interference error should be selected.

Once the selection of the absorption line(s), scan range and optional burst have been decided, the employment of the correlation or convolution with the kernel can be implemented.

In some signal processing applications, a filtered signal is obtained by correlating a known signal, profile, or template (referred to previously and from now on as the "kernel") with the signal to be analyzed, and the output omits or is less affected by unwanted parts of the signal. Such filters are sometimes known as a matched or shape filter. The kernel can be correlated with the unfiltered signal to produce a filtered signal with reduced noise, as the filter preferentially passes those parts of the signal that correlate well with the kernel. Such an approach was pioneered by D. O. North (Proc. IEEE 51, 1016-1027 (1963)). Another example of a convolution filter is the Savitzky-Golay filter (Savitzky, A., Golay M. J. E. (1964) Analytical Chemistry 36 (8): 1627-39). This is a linear, least squares, digital filter that can be applied to a set of data points for the purpose of smoothing the data. This is used to increase the signal to noise ratio within the signal.

The inventors of the present invention have proposed correlating a detected signal with a kernel that has a predefined, similar shape to a predicted signal or signal component, or correlating with a kernel that is selected to avoid or reduce the impact of predicted signal components. This is equivalent to convolving the detector signal with a time-reversed version of the kernel. In the case of the kernel being symmetrical, then correlation is identical to convolution. The correlation filter is an effective linear filter for optimising the signal to noise ratio (SNR) in the presence of additive random noise. The choice of the optimum kernel to use can be based on a predicted feature in the signal, which is desired to be extracted. As with any signal processing, manipulation of the signal may distort the processed signal from its "true" shape, but the correlation or convolution can reduce overall effect of distortions by reducing the effect of fluctuations such as optical interference effects on a signal baseline.

A correlation or convolution filter technique can be applied where random or unpredictable noise is present on the baseline of the signal. In this case, the optimum processed signal is obtained by using a kernel tuned to the shape of the feature that is desired to be extracted from the signal. This can also be helpful when no prior knowledge is available for the nature of the baseline noise. Conventional low pass (or high pass or bandpass) filters ideally apply gain equally to all passed frequencies, but the kernel used in this convolution technique applies preferential, non-linear gains to particular frequencies to enhance the desired signal shape relative to the baseline noise.

The inventors of the present invention have determined that a further optimization is achievable in absorption spectroscopy applications, when the distortions on the signal baseline include predictable signal components. Instead of developing a kernel purely based on the primary (measurand) signal to distinguish it from baseline noise by maximising its signal contribution relative to the baseline, a kernel corresponding to a component of the baseline noise (i.e. the fluctuations or distortions in the baseline) is developed. This "baseline" kernel can be chosen for either maximising the signal due to the baseline fluctuations in order to identify these effects and enable production of the "corrected" baseline with the distortion subtracted, or chosen such as to systematically minimise the relative influence of baseline distortions on the processed output. As an optional process, the kernel may also be adapted or a second kernel applied to also allow optimisation of the primary absorption measurement. This approach is only possible if it is possible to predict some characteristic of the baseline distortion profile, and will not be generally applicable in other applications.

This approach has merit for reducing the effects of noise in absorption spectroscopy systems due to the particular nature of the noise exhibited in such systems. Random noise can be reduced by use of a kernel function matched to the main absorption signal, and the effect of predictable signal distortions can be reduced by convolution with a kernel function that is matched to the predicted distortions. For example, optical interference effects may take the form of sinusoidal or pseudo-sinusoidal oscillations on the baseline, whose position and frequency may change with ambient conditions (sample composition, temperature, pressure, vibrations etc.). Since these oscillations have identifiable shape characteristics, they can be treated with a correlation or convolution filter in their own right.

In addition, the frequency range of these oscillatory features is of importance in deciding which kernel function to choose, and in particular when to use a kernel function that targets the baseline signal oscillations. If the frequency of oscillation is very high, it could be treated as pseudo-random noise, since their average effect would tend to zero. If the frequency is very low, it should have very little impact on the signal, since it would appear as a slowly changing offset underneath the signal. In both of these high frequency and low frequency cases, a correlation or convolution filter applied to the primary signal would prove the best approach. Likewise, if the baseline oscillations contain frequency components which strongly co-incide with the frequency components of the primary signal, it would prove potentially difficult to distinguish and extract the baseline feature from the primary feature. In the time domain, the more similar the baseline and primary measurand shapes or features become, the harder it is to separate out the two. Thus, the matching of a kernel function to predictable distortions, which will now be described in more detail, is most advantageous for interference or distortion of the baseline signal with periodic or pseudo-periodic characteristics within a particular frequency range or ranges. In this case, by periodic, it is meant a periodically occurring baseline feature within a single scan and also where the baseline feature occurs over multiple scans.

Oscillations caused by factors other than optical interference will also benefit from this approach, provided that there are repeatable, periodic shape features within the baseline distortions. For example, in recent work by the inventors, it was found that the laser residual amplitude modulation (RAM) signal at the laser modulation frequency was insufficiently attenuated by the correlation or convolution filter. Therefore, an additional adjustment to the correlation or convolution filter was made to filter for this effect as well, effectively acting as a notch filter at the laser modulation frequency.

Ideally, sufficient time scale within a scan should be present, such that at least some of the scan occurs where no primary absorption feature or burst feature is present, this may enable a cleaner determination of the true baseline. In addition, it is useful for at least one period of baseline oscillation to occur within the time frame analysed, since this helps the determination of frequency information.

It will also become apparent that, although this technique may be conducted in the time domain, it may advantageously be applicable in the frequency or Fourier domain and where the distortions occur within a relatively narrow frequency range. This frequency range will depend on the measurement system considered and the frequencies of the baseline distortions and primary measurand features to be measured.

Note that since the relative amplitudes of the primary signal and baseline distortion typically have no causal link, processing in the frequency domain also has advantages in distinguishing between the primary and baseline distortions through frequency discrimination.

Note also that although cleaning the baseline of distortion may allow more accurate determination of the measurand concentration which is present, in many cases, the application may be measuring where little or no measurand is present. Any implemented software will often include a peak and trough detection to detect the primary absorption peak and any distortions or oscillations in the baseline which protrude above the random baseline noise may give rise to false measurand readings when little or no measurand is present. In this case, the baseline kernel is pivotal in rejecting false detection of measurand absorption peaks and/or reduction in generic background noise limiting the "zero" signal and hence minimal detection limits.

As an illustration of implementation in the digital domain, the convolution or correlation operation consists of "sliding" the kernel (in the form of a data array) over the detector signal (in the form of a data array), moving it by one sample each time, and computing a new sample value for the output. The input samples covered by the kernel are multiplied by the corresponding entries (weights) in the kernel, and summed up. The kernel signal itself is often much shorter in duration than the input signal and is specified in the form of an N-element vector or array of numeric values.

As the kernel signal needs to slide along a whole set of input data, in the case of a finite input data set x[n] and for a 2N-element kernel, there will be N−1 samples at the beginning and end of the input data that do not have the required number of neighbours. This is sometimes referred to as the "edge problem" in convolution. There are numerous methods which may be used to minimise the edge effects in convolution such as zero padding or window function multipliers. However zero padding on either side of the finite input data set is one of the simplest techniques and will be used in the following illustrations. Zero padding in time domain has the important benefit that it does not in any way alter the frequency content of the original data and in wavelength modulated spectroscopy (WMS) this is a highly important benefit.

Figure 5:
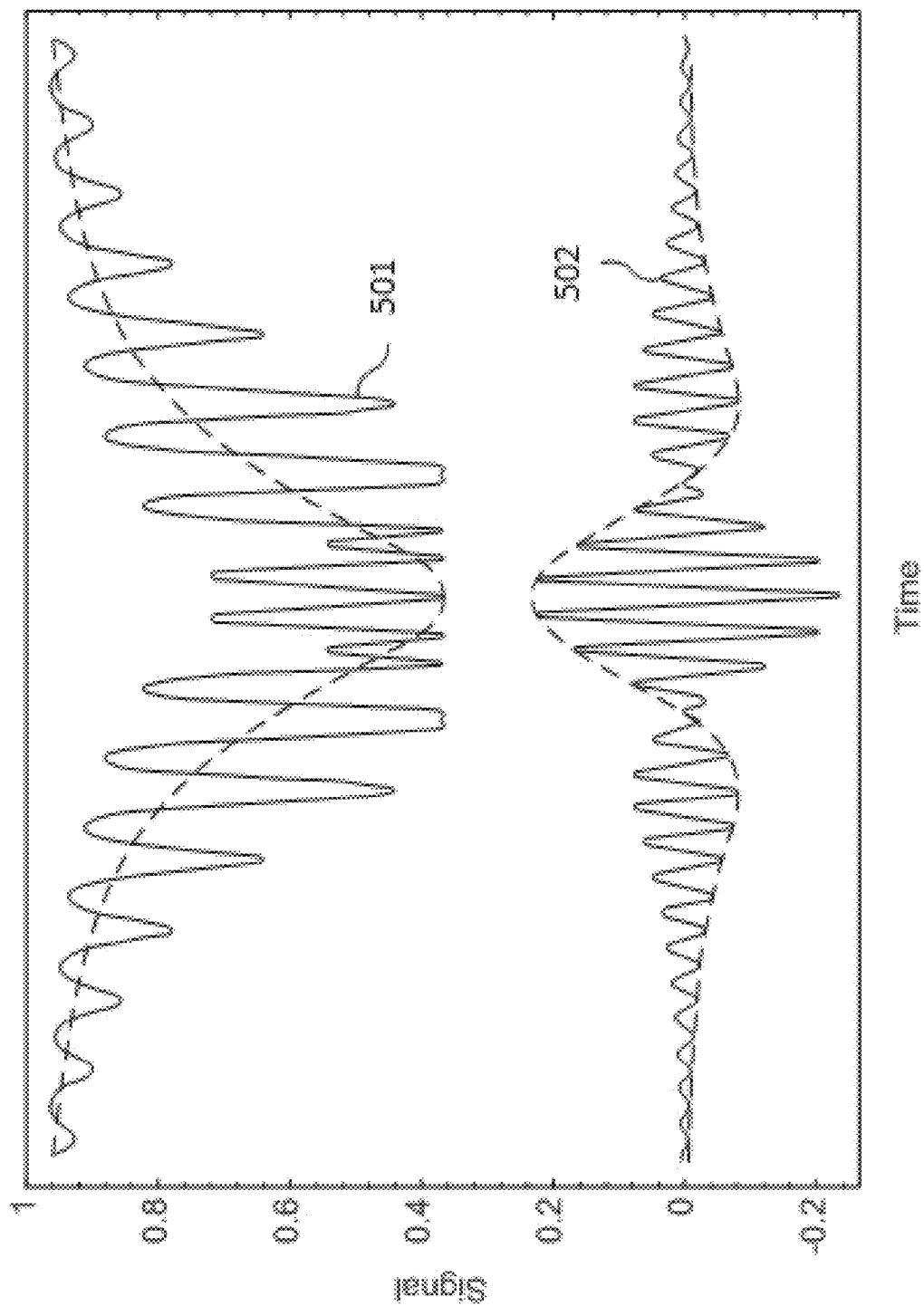
FIG. 5 is a plot of signal versus time for a TDLS system also with the demodulated (second harmonic) signal shown.

In practical TDLS applications using second harmonic wavelength modulation techniques, the gas absorption signal (501) appears at the detector as a $2^{nd}$ harmonic signal (502) shown in FIG. 5.

Figure 6:
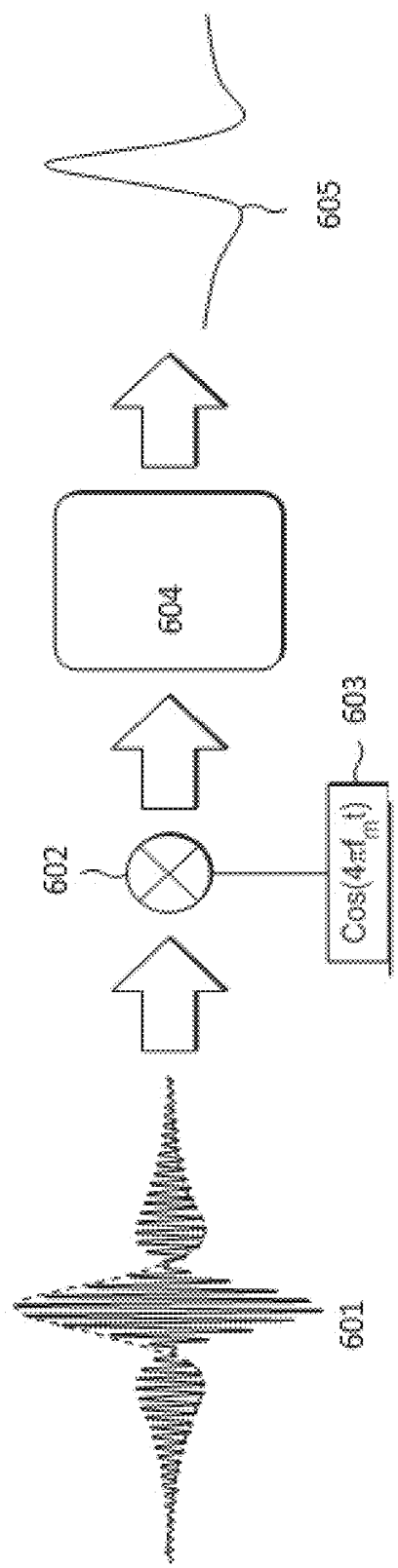
FIG. 6 is an illustration of the demodulation method.

The processing of the $2^{nd}$ harmonic signal is illustrated in FIG. 6. In a conventional lock-in amplifier, the $2^{nd}$ harmonic signal (601) is subsequently demodulated (602) in software by the 2f reference sine wave (603) which is then filtered using a conventional multi-stage averaging filter (digital filter) (604) to produce the envelope of the second harmonic signal (605).

The most commonly used averaging filter is a multi-stage low pass filter with a fixed or adjustable cut-off frequency which aims to suppress the unwanted parts of the signal. However, the limitations of conventional low-pass (or high pass or bandpass) filtering need to be considered:

Low pass (or high pass or bandpass) filters do not know anything about the overall shape of the receiver signal, such as the shape features of the baseline distortions, absorption profiles or 2f bursts.

Low pass (or high pass or bandpass) filters do not know anything about the neighbourhood of values. They apply suppression equally across all features of a shape.

In order to enhance or manipulate the dynamic features of a shape, it is required to step beyond the conventional filtering operations. In contrast to the above-described conventional low-pass (or high pass or bandpass) filters, correlation or convolution filters can be used in applications where:

a signal must be detected in the presence of large additive noise.

and the receiver has a knowledge of what signal shape it is looking for.

In exemplary embodiments of the present invention, correlation or convolution filters are implemented by correlating the receiver signal to a known template or kernel shape to identify features in the signal that are common to that kernel. The process of correlation for symmetrical kernels may be implemented mathematically by the convolution technique.

The convolution operation consists of "sliding" the Kernel shape h[n] over the entire length of the detector signal x[n], moving it one sample at a time, and computing a new value by multiplying and integrating over the length of the Kernel M.

$$(h*x)[n]=\Sigma_{m=0}^{M}h[n-m]\cdot x[m] \qquad [3]$$

The inventors have determined that TDLS applications can make use of a form of filtering that differs, in preferred embodiments, from conventional matched filters. This is because the Lorentzian, Gaussian or Voigt harmonic shapes of typical gas absorption lines are distinct, symmetrical and clearly identifiable in the midst of random baseline signals that may be present in a real application. However, in addition, sinusoidal or pseudo-sinusoidal or other periodic baseline distortions, which may also be present, can also be distinguished from random or stochastic baseline noise. In the case of sinusoidal or additive sinusoidal distortion, analysis in the frequency domain is particularly advantageous due to the simplicity of the resultant frequency spectrum, where each sinusoidal component will result in a single frequency component in the frequency (Fourier) domain.

The baseline kernel chosen may be sinusoidal, pseudo-sinusoidal or another defined shape derived theoretically, empirically or through a combination of both, corresponding to the shape or inverse shape of the distortion pattern on the baseline.

The form of the baseline kernel may be chosen to determine the baseline distortion and hence to derive the corrected baseline noise or chosen so as to reduce the impact of the periodic distortion on the measured signal. In some applications, the analysis may be switched between these two modes, if, for example, it is found that under certain circumstances, such as in conditions of very low levels of measurand being present in the sample, one mode gives a better signal to noise ratio.

Illustrations will now be given of methods to determine the optimal kernels in order to implement the optimum correlation or convolution filter, taking the baseline distortions into account for the kernel.

In one embodiment, the first stage of the method is to study the baseline noise, preferably with no measurand present, for example by flushing the measurement system with a non-absorbing sample in the wavelength range of interest, but in a representative arrangement of the final measurement configuration such that any periodic baseline distortions are representative of what would be seen in its intended application, i.e. preferably including all of the relevant optical elements and mounting arrangements. The baseline kernel is then derived and this process is described in more detail later.

Once this has kernel been determined and verified, a second adaptation to the baseline kernel or secondary kernel may be (optionally) derived to tune for the absorption line shape or other feature required to be determined.

Note this combined kernel may then be further modified to optimise for the best compromise between minimising the baseline fluctuation influence and maximising the absorption signal.

This resultant kernel is then used in a convolution procedure or procedures to produce the required analysis. This process will be described in more detail below.

In one embodiment, designed to minimise the baseline distortion and maximise the absorption signal, the first stage of the method is for the kernel to be tuned for the absorption line shape or other feature required to be determined.

Once this has kernel been determined and verified, a second adaptation to the baseline kernel or secondary kernel is applied.

The baseline noise is then studied, preferably with no measurand present, but in a representative arrangement of the final measurement configuration such that any periodic baseline distortions are representative of what would be seen in its intended application, i.e. preferably including all of the relevant optical elements and mounting arrangements.

The baseline kernel is then derived and this process is described in more detail later. The original kernel is then adapted to give the combined kernel.

Note this combined kernel may then be further modified to optimise for the best compromise between minimising the baseline fluctuation influence and maximising the absorption signal.

This resultant kernel is then used in a convolution procedure or procedures to produce the required analysis. This process will be described in more detail below.

In one embodiment, a kernel is chosen which is based on the shape of the fluctuation pattern on the baseline. The baseline noise is studied, preferably with no measurand present, but in a representative arrangement of the final measurement configuration such that any periodic baseline distortions are representative of what would be seen in its intended application, i.e. preferably including all of the relevant optical elements and mounting arrangements. The baseline kernel will then be derived and this process is described in more detail later.

The processed baseline profile is then determined by correlation or convolution with the kernel.

The processed baseline signal is then subtracted from the original signal in order to provide a corrected net signal, where the baseline has been cleaned up from systematic noise.

This resultant signal may now be analysed for any absorption signal, which may be present, thus enhancing sensitivity.

In one embodiment, a kernel is chosen which is based on the inverse shape of the fluctuation pattern on the baseline. The baseline noise is studied, preferably with no measurand present, but in a representative arrangement of the final measurement configuration such that any periodic baseline distortions are representative of what would be seen in its intended application, i.e. preferably including all of the relevant optical elements and mounting arrangements. The inverse baseline kernel (mirror image of the previous kernel illustrated) will then be derived and this process is described in more detail later.

The processed inverse baseline profile is then determined by correlation or convolution with the kernel.

The inverse processed baseline signal is then added to the original signal in order to provide a corrected net signal, where the baseline has been cleaned up of systematic noise.

This resultant signal may now be analysed for any absorption signal, which may be present, thus enhancing sensitivity.

For whichever method is used, the resultant kernel may then be used in a convolution procedure or procedures to produce the required analysis. The process of deriving kernels and implementing convolution, and the resultant signal, will be illustrated in more detail below.

The kernel shape for the primary measurand absorption signal may be optimally chosen to have a shape corresponding to the expected absorption line shape such as, Lorentzian (collisional (pressure) broadening regime), Gaussian (Doppler broadening regime) or Voigt (combination of the previous two) profile, although other shapes may be selected for empirical or other reasons. The origins of these theoretical absorption profiles are known to those skilled in the art and will not be discussed further here.

The preferred kernel shape may be influenced by the gas to be measured and the ambient conditions such as background gas, temperature and pressure. In some instances, the preferred kernel shape to be used for a specific measurand will change in accordance with ambient conditions such as from a low temperature, high pressure ambient (Lorentzian) kernel to the use of a high temperature, low pressure (Gaussian) kernel and a Voigt kernel for the intermediate zone.

In some specific instances the kernel shape may correspond to a compound absorption line, such as a doublet or triplet or higher order.

The kernel shape may also be derived empirically, theoretically or a combination of both.

The kernel may also be a combination of two or more of the shape functions described above.

The following is a more detailed illustration of the implementation of this technique. This is an illustration of minimising the relative impact of the baseline distortions on the signal by generating a compound kernel both to suppress the baseline distortions and to enhance the absorption profile of the measurand. In this case, optical interference effects (etalons) are present on the baseline, but the invention is generally applicable for periodic distortions of whichever origin.

Figure 7:
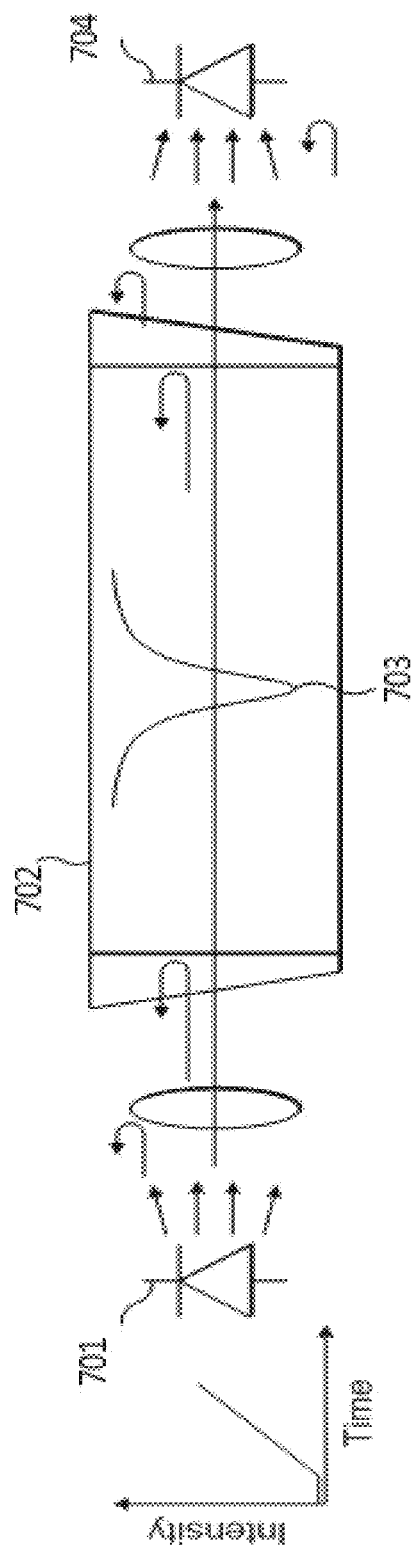
FIG. 7 is an illustration of where optical interference may occur in a TDLS measurement.

The advantages of using tunable diode laser absorption spectroscopy (TDLS) for trace gas sensing include fast response times, high sensitivity and high target gas selectivity. However, the performance of many practical TDLS systems may be limited by the formation of unintentional Fabry-Perot type optical interference in the optical path between the source (701) and detector (704) (FIG. 7). In many applications the formation of this interference can lead to distortion or even complete obscuration of the shape of the absorption line. Thermal and mechanical variations in a real field instrument mean that the baseline oscillations cannot be removed by simple subtraction techniques, as described earlier. FIG. 7 shows, by curved arrows, typical areas where optical interferences can occur, such as at sample cell (702) windows, although they may form due to any reflective interface. There are numerous design techniques, optical, electronic and mechanical, to reduce the magnitude of this interference. However, even after all measures are used, a residual amount of interference remains, resulting in fluctuations on the baseline affecting the resolution of the absorption line (703), which may be improved with by the use of the correlation or convolution filters described herein.

The convolution technique may be used for a variety of kernel shapes in the time or frequency domain, however, specific illustration will now be given to the advantages of the application of the convolution technique in the Fourier domain.

The basic mathematical theory of convolution states that: Convolution of two signals in spatial or time domain is equivalent to multiplication of their Fourier transforms in frequency domain, this is mathematically stated as follows:

$$F[g*h]=F[g]F[h] \qquad [4]$$

Therefore, by then performing an inverse Fourier transform on the product, the filter output may be obtained.

Performing correlation functions in the time domain is computationally intensive. For a signal of length N and a kernel of length K, they require about N*K operations (multiplications and additions). Typically, for the application illustrated, the signal is 2,000 points long and the shape that sought uses a kernel about 500 points long, implying that about 1,000,000 operations per frame, bearing in mind that hundreds or thousands of frames may be acquired each second. In the frequency domain, only the low frequency components are of interest and must be multiplied, since the kernel contains no high frequency content, and so only the lower elements of the Fourier transform are non-zero.

By ignoring the high frequency components, only about 150 multiplication operations need to be performed, instead of N*K operations and the other values are assumed to be zero. This illustrates the convolution process acting as a low pass filter, since only the lower frequencies have non-zero values. However, the signal Fourier transform and inverse Fourier transform must be performed in real time. For a fixed kernel, its Fourier transform need only be calculated once, since it is constant. Generally, a discrete Fourier transform (DFT) requires about $N^2$ operations, which for our above example, implies 4,000,000 operations. However, this may be reduced by using fast Fourier transform (FFT) algorithms. This reduces the number of operations to $N*\log_2 N$ if N is equal to 2 raised to some integer power. If this condition is satisfied via e.g. zero padding i.e. up to 2,048 ($=2^{11}$) for both the signal and kernel, in this example, the Fourier transform operations have been reduced to 22,528 (=2,048*11). The end result is that the correlation is obtained in about 45,000 operations (22,528 in each direction of the Fourier transform process) using the frequency domain as opposed to using the time domain with 1,000,000 operations or more, which is over twenty times faster. Furthermore, modern microprocessors have dedicated floating-point unit (FPU) cores that are specifically designed to accomplish such calculations very efficiently.

Figure 8:
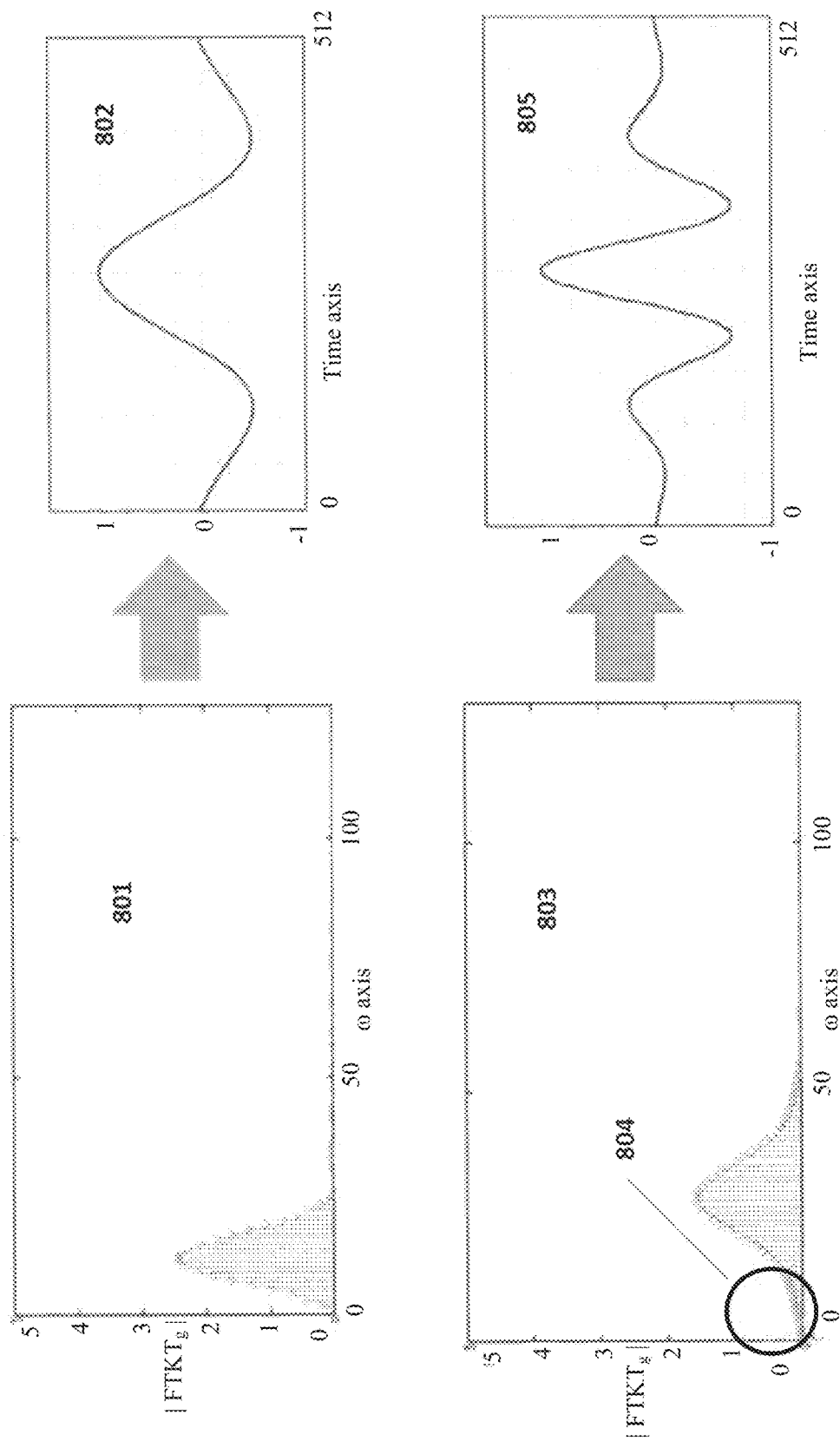
FIG. 8 shows a comparison between a simple kernel designed purely to recover the $2^{nd}$ harmonic Lorentzian gas signal and a more sophisticated kernel designed both to suppress optical interference and to recover the gas signal.

In some practical TDLS applications, with undesired baseline distortion such as due to optical interference, it is not sufficient for the kernel only to enhance the absorption shape of the gas signal. It is also of primary importance to give the kernel the ability to actively suppress the optical interference distortions on the baseline. For example, many optical interferences caused by undesired cavities or spurious reflections typically produce sinusoidal baseline fluctuations of varying frequencies. In the frequency domain, these may appear as single Fourier terms with no or little correlation to the kernel overall shape. If the location of these optical interference frequency components is near the lower ω axis (low frequency), this can be mitigated by a convolution with a kernel function whose frequency spectrum has been transformed to higher frequencies in order to eliminate or reduce low frequency interference. In this way, the kernel function is adapted to transform the frequency spectrum of the predicted absorption signal feature to a higher frequency to isolate the predicted absorption signal feature from frequency-specific distortions of the indicative signal. Likewise, if the location of these optical interference frequency components is near the higher ω axis (high frequency), this can be mitigated by a convolution with a kernel function whose frequency spectrum has been transformed to lower frequencies in order to eliminate or reduce high frequency interference. In this way, the kernel function is adapted to transform the frequency spectrum of the predicted absorption signal feature to a lower frequency to isolate the predicted absorption signal feature from frequency-specific distortions of the indicative signal. This shift in the frequency spectrum of the features of interest, via selection of kernel coefficients, has a direct impact on the shape of the kernel in the time domain. Indeed, even if processing is carried out in the time domain, it may be easier to derive the optimal compound kernel in the frequency domain and then create the time domain kernel via an inverse Fourier transform. FIG. 8 shows a Lorentzian kernel (801 and 802) designed purely to recover the $2^{nd}$ harmonic Lorentzian gas signal. This is illustrated in the frequency or Fourier domain as 801 and the same kernel is shown in the time domain as 802. A more sophisticated kernel (803 and 805) designed both to suppress optical interference distortions on the baseline and also to recover the gas absorption signal is also illustrated. This is shown as 803 in the frequency or Fourier domain and the same kernel is illustrated in the time domain as 805. Note the clear stretching and the oscillatory wing behaviour of the second kernel, as the convolution operation is not merely a matched filter. It should be noted that a compromise must be reached for the optimum kernel between suppression of the low frequency optical interference effects (in this case) (804) and retention of the absorption signal without too much signal loss or distortion. It is not simply a method for eliminating the baseline distortion completely and maximising the absorption signal by a conventional matched shape filter, but instead applies a frequency-selective variable gain that selectively suppresses identified or predicted distortions on the signal baseline and enhances the required part of the signal relative to noise.

In some applications, such as the determination of trace gases as impurities in a sample or continuous emissions monitoring (CEM) for pollution control, the measurand concentration may be zero or almost zero most of the time. In these instances, the noise on the signal will be dominated by the baseline noise. Implementation of a signal kernel such as a Lorentzian will be of limited use when there is little or no absorption occurring. Instead, a kernel may be chosen which is the shape of the interference pattern on the baseline, namely a sinusoidal, pseudo-sinusoidal or other defined shape derived empirically, theoretically or combined such that the "signal" sought becomes the baseline pattern itself. The baseline profile is then determined by correlation or convolution and subtracted from the original signal in order to provide a net signal, where the baseline has been cleaned up. This resultant signal may now be analysed for any absorption signal, which may be present, thus enhancing sensitivity. An equivalent technique may be applied whereby the inverse kernel of the optical interference pattern on the baseline is used instead to determine the inverse baseline signal and then this inverse signal is added to the baseline to produce a cleaned up baseline signal which may then be analysed for any absorption occurring. This functional mode for low level signals may be switched off and on either manually or automatically if required. For example, when the measurand concentration has exceeded a pre-determined threshold, the signal processing kernel could revert to a standard absorption line format such as Lorentzian, Gaussian or Voigt profile. By such means, the uncertainty in the measurand determination is reduced.

Figure 9:
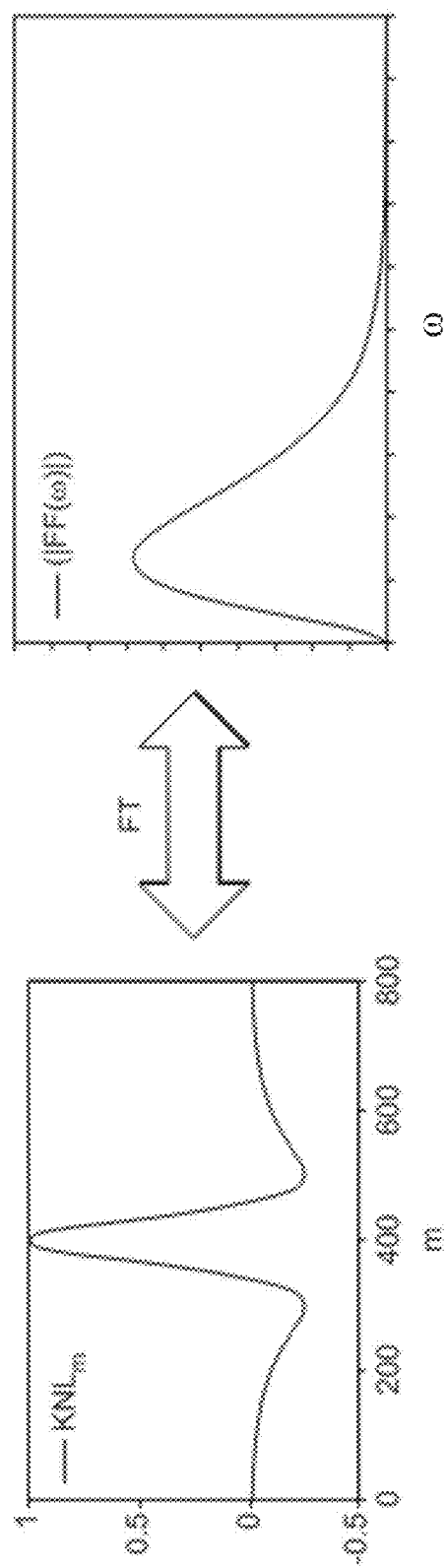
FIG. 9 is an illustration of the Fourier transform of a Lorentzian line shape.

Some thought will now be given to the shape of the primary absorption signal to be determined. The unique shape of the $2^{nd}$ harmonic signal in time domain leads to a unique shape for the Fourier coefficients in frequency domain (FIG. 9). For example, the Fourier transform equation of the $2^{nd}$ harmonic Lorentzian has extremely important properties, which emphasizes the power of kernel analysis. If the kernel width is $\delta k$ and the gas width is $\delta g$, then the convolution of a $2^{nd}$ harmonic kernel with a $2^{nd}$ harmonic gas signal produces the following Fourier product:

$$(\pi \cdot \omega^2 \cdot e^{-\delta k \cdot \omega})(\pi \cdot \omega^2 \cdot e^{-\delta g \cdot \omega}) = (\pi^2 \cdot \omega^4 \cdot e^{-\omega \cdot (\delta g + \delta k)}) \quad [5]$$

The product on the right-hand side of the above equation can be re-written as:

$$(\pi^2 \cdot \omega^4 \cdot e^{-\omega \cdot (\delta g + \delta k)}) = \pi \cdot \omega^2 [\pi \omega^2 \cdot e^{-(\delta g + \delta k) \cdot \omega}] \quad [6]$$

Note that the term on the right of equation [6] is a $2^{nd}$ harmonic Lorentzian of width ($\delta g + \delta k$). Therefore, convolving a $2^{nd}$ harmonic Lorentzian kernel with a $2^{nd}$ harmonic gas signal produces another $2^{nd}$ harmonic Lorentzian signal of a wider width. This is a highly significant result showing that in TDLS applications, the kernel convolution has a strong ability to enhance the $2^{nd}$ harmonic signal. Since the width of the kernel $\delta k$ is known, the width of the absorption line $\delta g$ may easily be derived. It is also clear that the product of the kernel Fourier transform with any other shape in frequency domain will not result in the general form of a $2^{nd}$ Lorentzian. This gives the convolution kernel a very strong shape distinction capability in TDLS which is not available from a conventional low pass (or high pass or bandpass) filter.

Typically, the kernel line-width is $\frac{1}{4}^{th}$ the value of the kernel length in order to ensure that the entire wings of the $2^{nd}$ harmonic Lorentzian shape are represented in the kernel window, although longer or shorter kernels are also possible.

Figure 10:
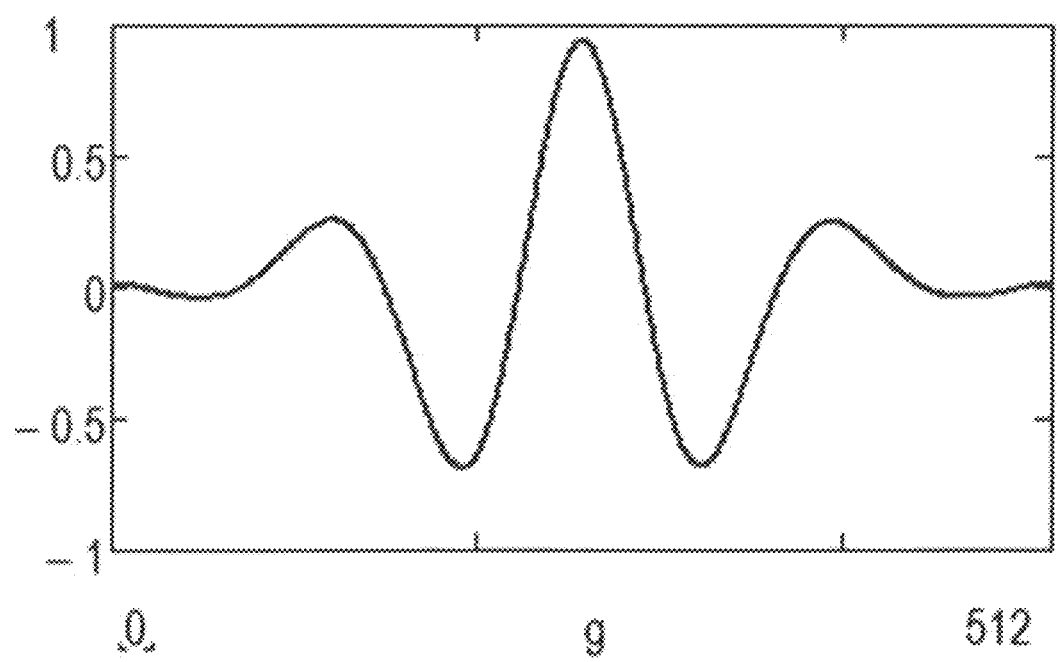
FIG. 10 shows a typical profile for the kernel function.

FIG. 10 shows a typical graph for the kernel function for a Lorentzian shape of length 512 points for a scan window of 2,000 points.

The convolution theorem states that convolution in the time domain corresponds to multiplication in the frequency domain. Therefore, the Fourier transform of the convolution of two signals is equal to the product of their individual Fourier transforms. The Fourier transform of a signal can be also evaluated computationally efficiently and quickly using the Fast Fourier Transform (FFT).

Figure 11:
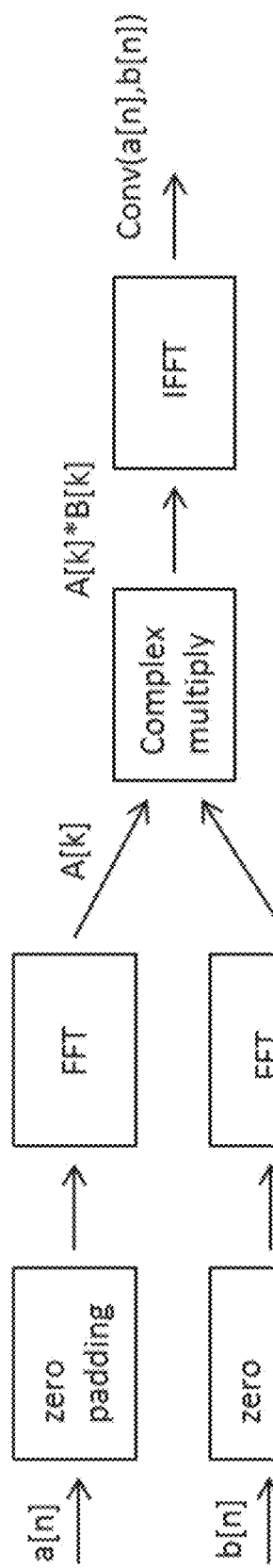
FIG. 11 shows the stages in the process to obtain the filter output.

Two input signals, a[n] and b[n], with lengths N1 and N2 respectively, are zero padded so that their lengths become N, which is greater than or equal to (N1+N2−1) and is a power of 4 as FFT implementation is radix-4. The convolution of a[n] and b[n] is obtained by taking the FFT of the input signals, multiplying the Fourier transforms of the two signals, and taking the inverse FFT of the multiplied result. This is denoted by the following equations:

$A[k]$=FFT($a[n]$) an $N$-point FFT $B[k]$=FFT($b[N]$) an $N$-point FFT $$\text{conv}(a[n],b[n])=\text{IFFT}(A[k]*B[k],N) \quad [7]$$

where A[k] and B[k] are the N-point FFTs of the signals a[n] and b[n] respectively. This process is illustrated in FIG. 11. The length of the convolved signal is (N1+N2−1). IFFT represents the inverse fast Fourier transform.

Figure 12:
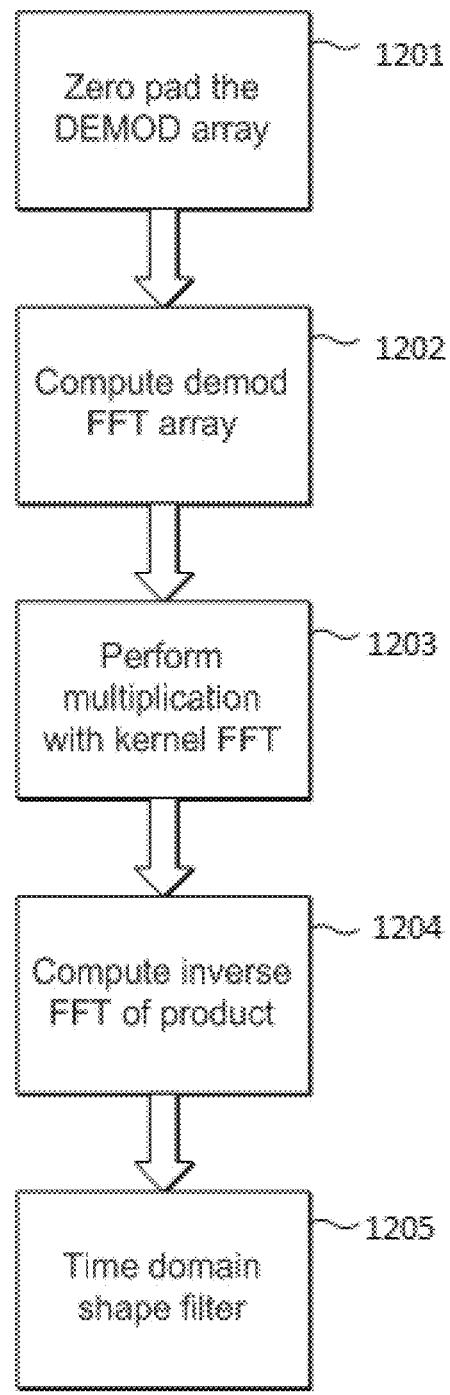
FIG. 12 shows the processes conceptually for obtaining the time domain convolution filter output.
Figure 13A:
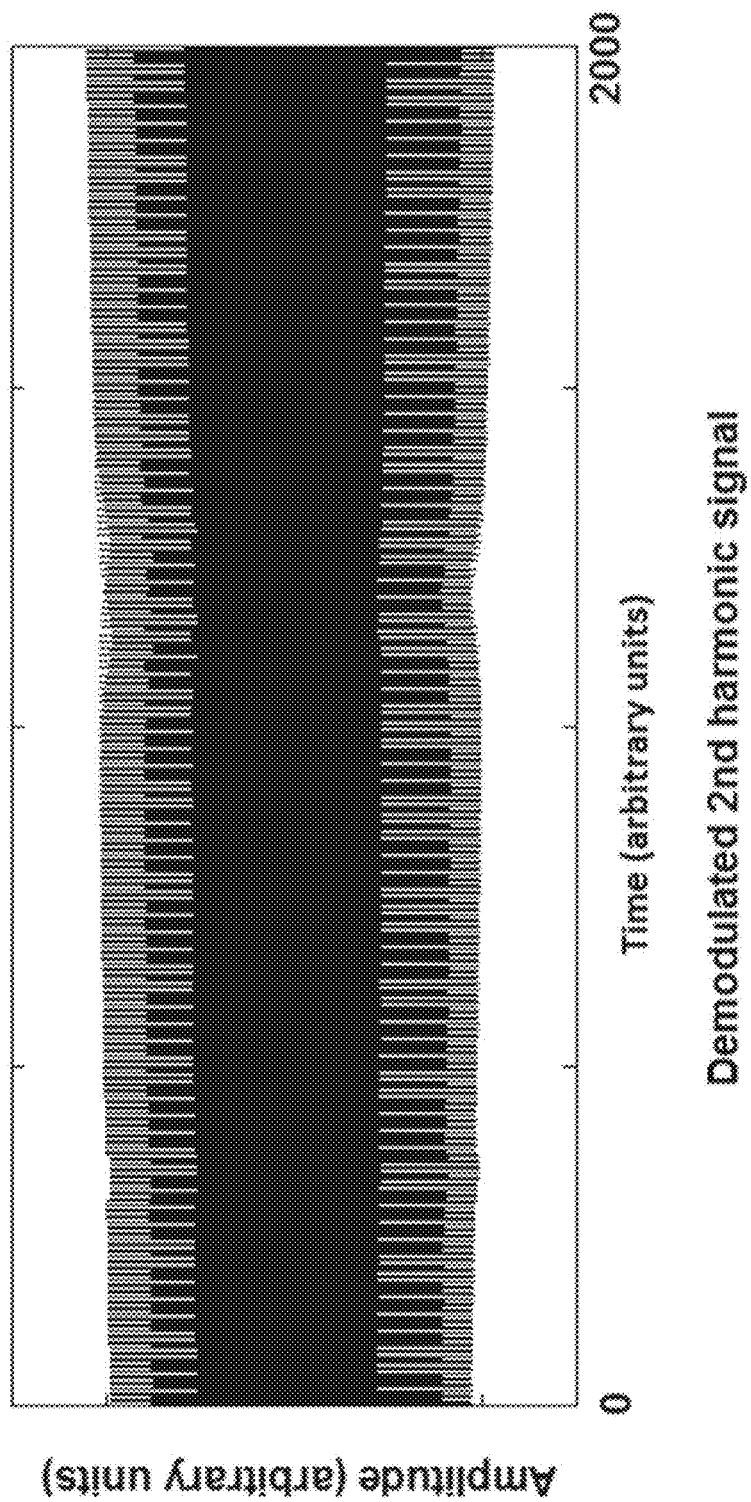
FIG. 13(*a*) shows the signal for a TDLS second harmonic system without zero padding applied.
Figure 13B:
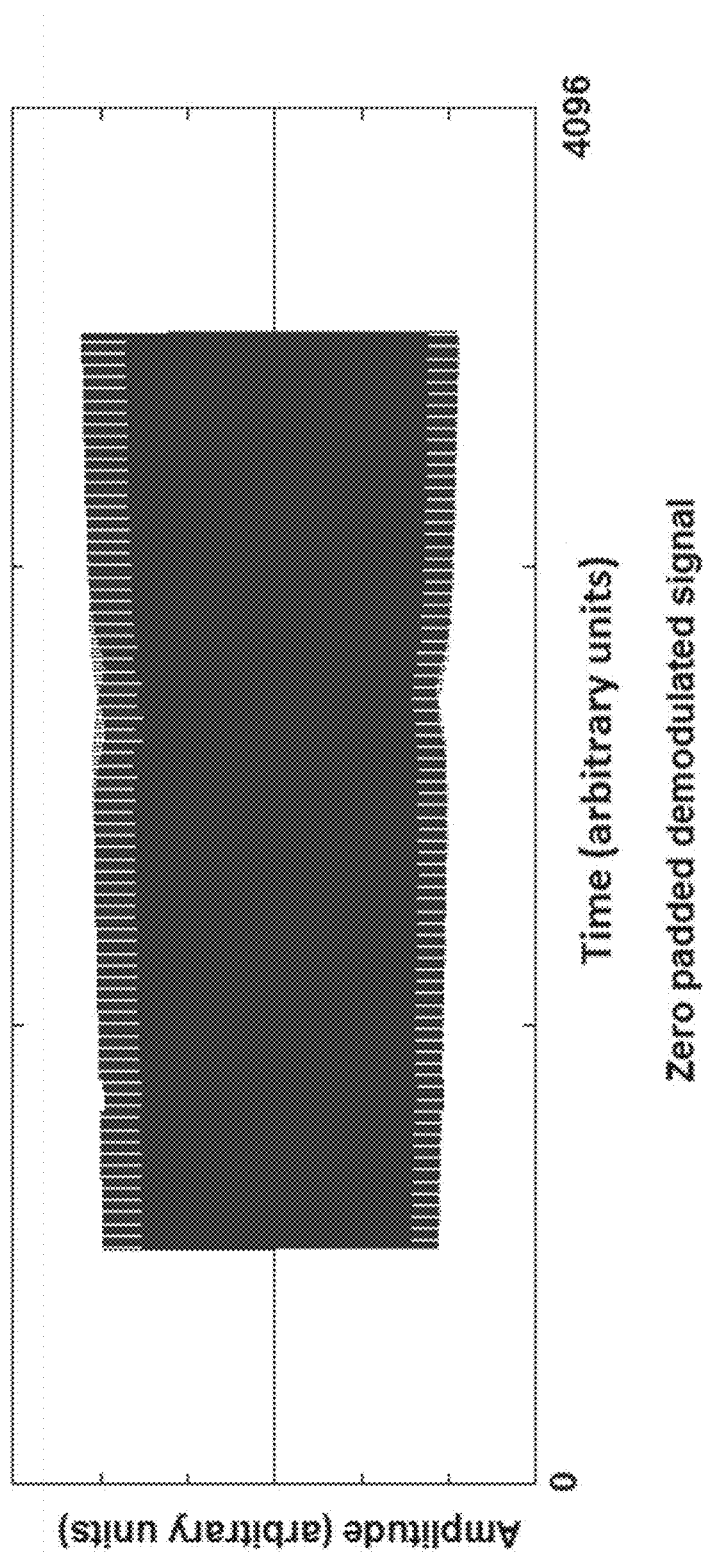

It is often convenient, but not a requirement, for demodulation at 2f to take place in the time domain before the convolution process and this may easily be accomplished using the methods described earlier and illustrated in FIG. 6. This demodulated time domain array will be called the DEMOD Array and used for further illustration. Zero padding of the DEMOD Array is done symmetrically at both the beginning and end segments of the DEMOD Array. Since FFT operations require a $2^n$ wide array, a typical 2000 point scan needs to be zero padded to at least 2048 ($2^{11}$). This process is illustrated in FIG. 12 stages 1201 to 1205. The array ZFF is the zero-padded array. FIGS. 13(a) and 13(b) show a typical DEMOD Array signal before and after zero padding respectively.

In performing the FFT product computation it is useful to limit the product computation to 128 Fourier coefficients. This simple restriction not only saves computation time, but also removes high frequency artefacts from the correlation or convolution filter when the inverse FFT is calculated.

Figure 14:
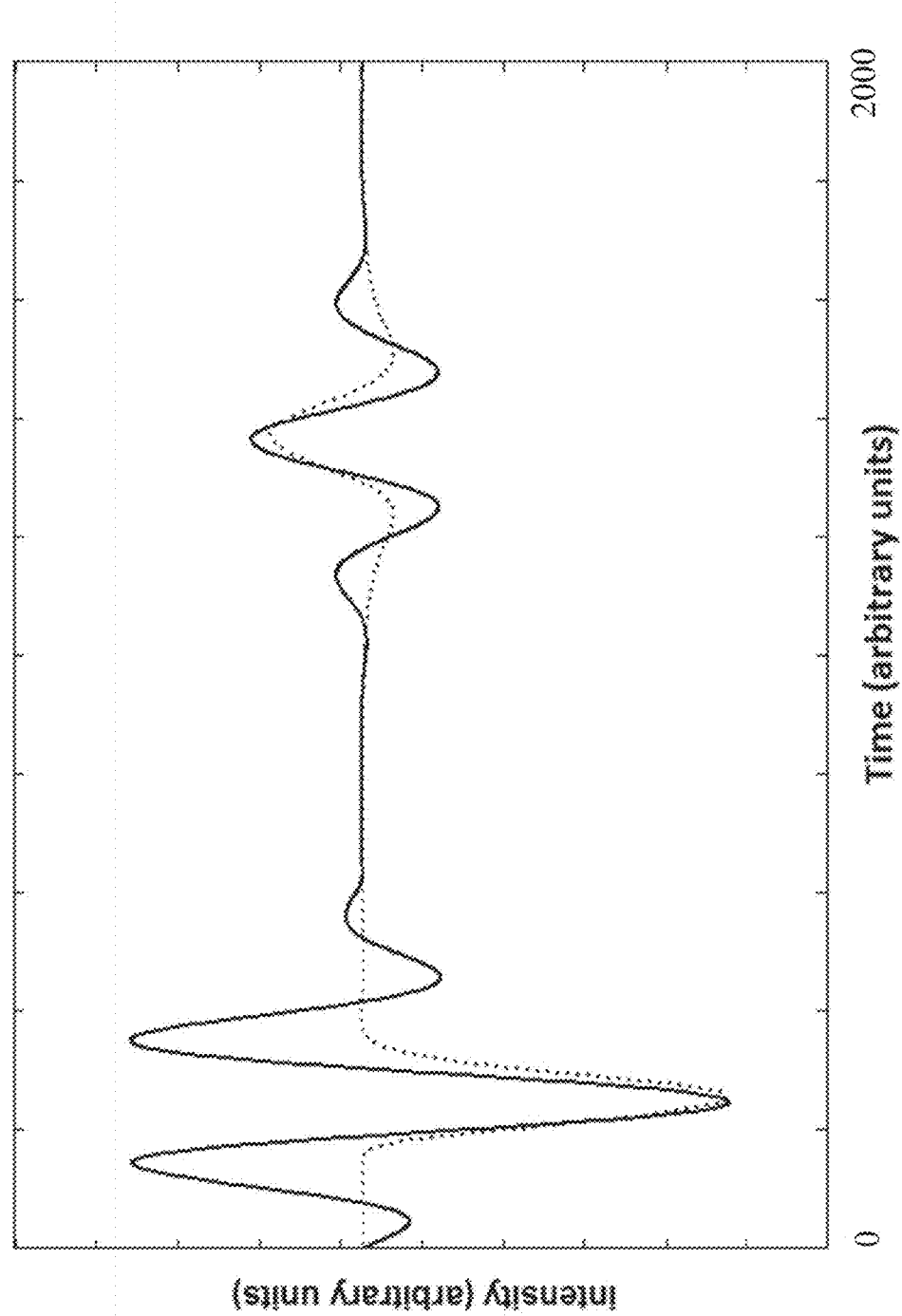
FIG. 14 shows simulated comparisons between the output for a TDLS second harmonic system of the (Lorentzian) convolution filter and the conventional Bessel filter.

By using a mathematical simulation software package, it is possible to perform simulated comparisons between the output of the correlation or convolution filter and the conventional Bessel filter. FIG. 14 shows such a comparison for a simulated Oxygen line (for ease of illustration, the offset shifts in the x axis due to processing have been removed for both filters). The striking difference between the two is in the shape of the 2f modulation. The 2f modulation acts as step response for the filter showing the overall shape of the underlying kernel. The first inverted peak in the figure is the induced 2f burst for intensity fluctuation compensation.

Figure 15:
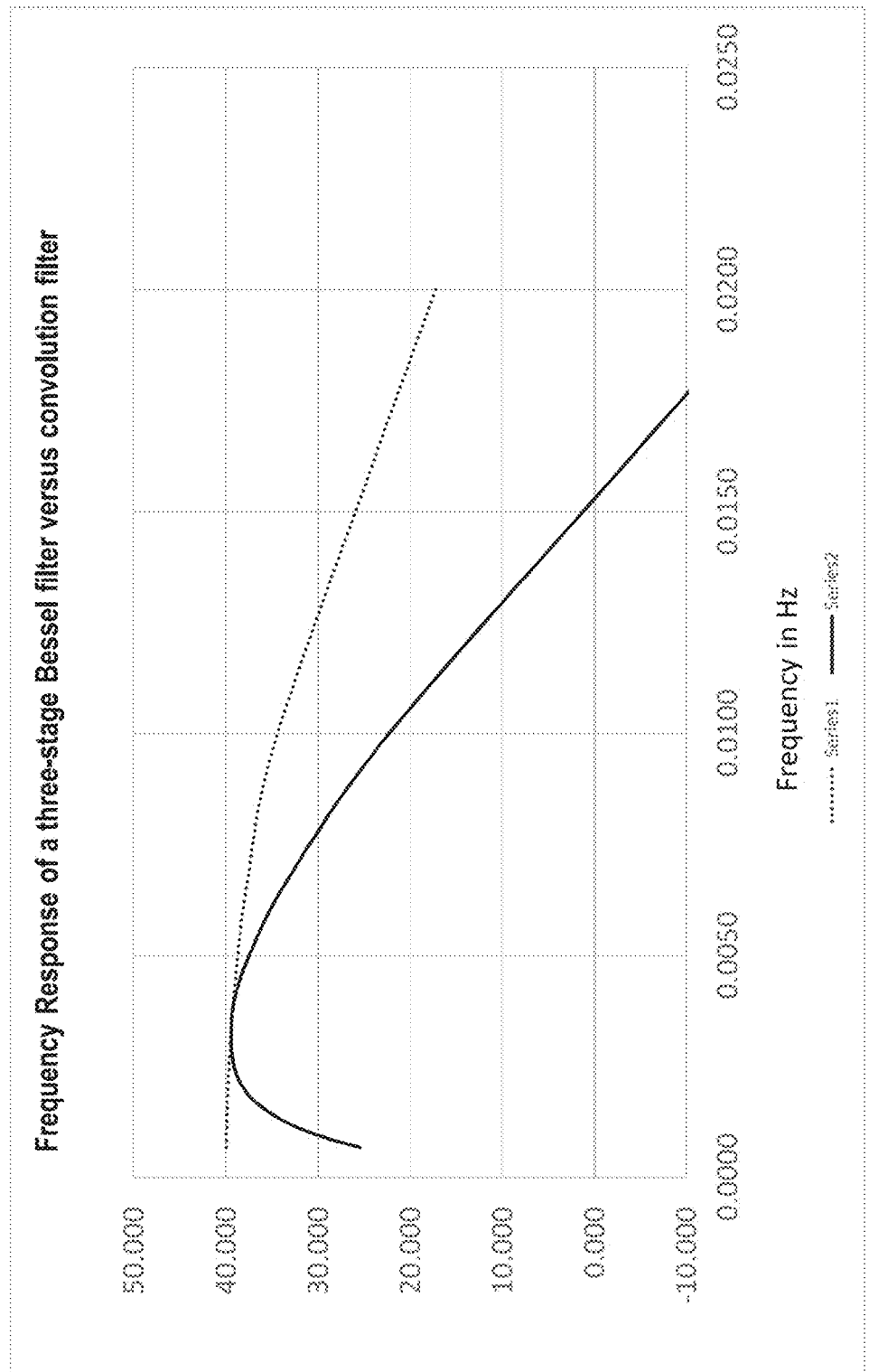
FIG. 15 shows the simulated frequency response comparison for a TDLS second harmonic system between a three stage Bessel filter and the (Lorentzian) convolution filter.

The frequency responses of the 3-stage Bessel filter (dotted line) and the correlation or convolution filter (solid line) may be simulated by normalising the results within a scan of a typical sine wave with varying frequencies. Using a software simulation, the plot in FIG. 15 clearly shows the differences in the two techniques:

a) The Bessel filter behaves like a normal low pass with flat response below the cut-off frequency and a decaying envelope above the cut-off frequency.

b) The correlation or convolution filter behaves as a frequency-dependent variable gain filter in the frequency domain with a decaying envelope both below and above the "pass-band". The decay envelope is much sharper than a conventional low pass filter. The rejection at low frequencies is very clear and this is the area where, for example, the optical interference attenuation is highly effective.

Figure 16:
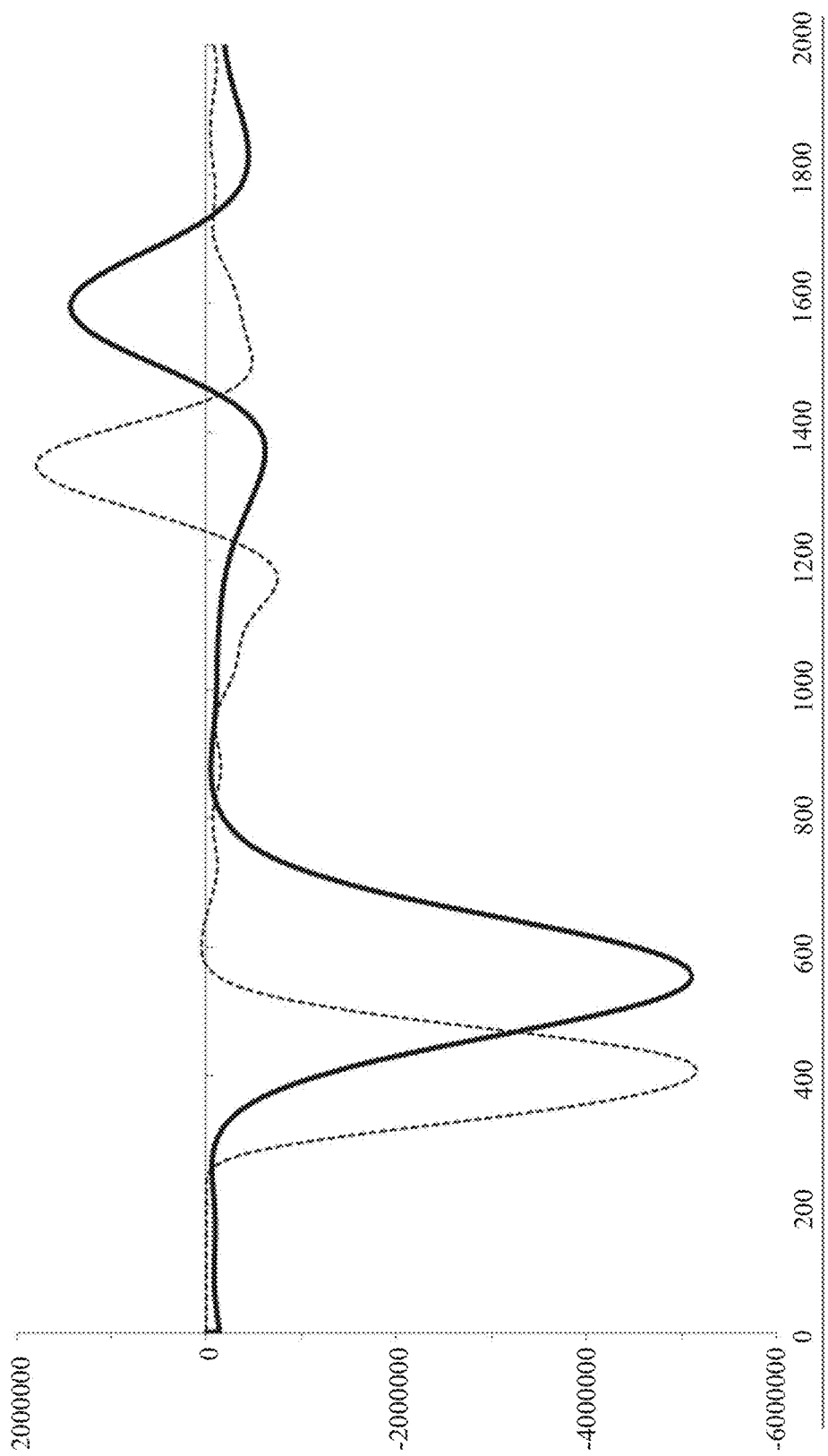
FIG. 16 shows an example using real data for a carbon monoxide measurement with a standard Bessel filter and with the convolution filter applied for a 2,000 ppm carbon monoxide in nitrogen measurement.
Figure 17:
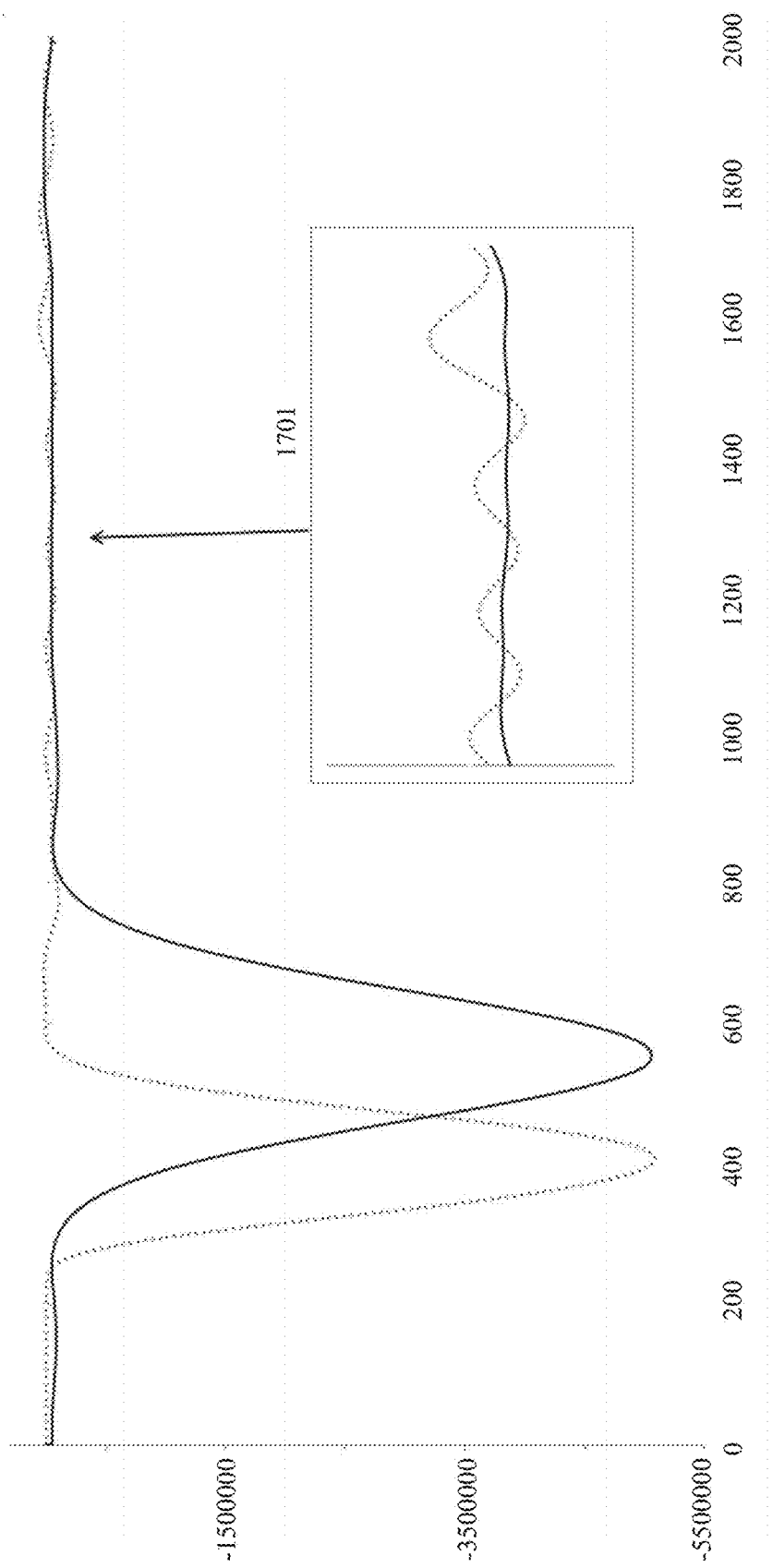
FIG. 17 shows an example using real data for a carbon monoxide measurement with a standard Bessel filter and with the convolution filter applied for a 0 ppm carbon monoxide in nitrogen measurement.

An example will now be given of the implementation in a real measurement. FIGS. 16 and 17 show scans for a tunable diode laser gas analyser designed to measure carbon monoxide (CO) in a sample gas. The measurement here has been made at ambient temperature (21° C.) and atmospheric pressure for a measurement path length of 50 cm. A CO absorption line has been selected at about 2.3 µm. The main cause of baseline distortion is optical interference from cell windows. In both figures, the inverted pulse on the far left of the graph is the 2f burst for intensity correction. The x-axis represents the scanned time and the y-axis the light intensity arriving at the detector. In both cases, the dotted line shows the standard low pass filter (Bessel filter) output and the solid line, the convolution filtered output. Note that there is a relative signal processing shift in the x axis between the two filter outputs. FIG. 16 shows the result for a sample gas containing 2,000 ppm CO in nitrogen and FIG. 17 shows the result for a sample gas with no CO present (nitrogen). Note in both cases the dramatic improvement (decrease) in the baseline fluctuations. This results in improved accuracy (decreased uncertainty) in the CO concentration determination (see close up (1701)). The 2,000 ppm CO peak in FIG. 16 illustrates the scale of baseline fluctuations and bearing in mind that the wavelength location of these fluctuations may change over time due to ambient condition changes, particularly temperature.

On closer examination of FIG. 16, it can be seen that the convolved or correlated CO peak height is actually smaller than the conventional low pass filter (Bessel filter) peak height relative to the burst signal. This reflects the fact, as discussed earlier, that a compromise must be reached between enhancing the absorption signal and minimising the impact of baseline distortion. Although the absolute peak height may have been reduced, the benefit derived from decreased baseline distortion more than compensates for the reduced peak height, so that the overall stability and signal to noise are significantly improved relative to a conventional (Bessel) filter output.

It will be appreciated by those skilled in the art that numerous modifications, adaptations and variations to the methods and embodiments described herein will become apparent having the benefit of the present disclosure, and such modifications, adaptations and variations are also embodiments of the present invention.

In addition to the claimed embodiments in the appended claims, the following is a list of additional embodiments which may serve as the basis for additional claims in this application or subsequent divisional applications:

Embodiment 1

A method for reducing the effects of distortions on the baseline of an absorption signal within an absorption spectroscopy system, comprising the steps of:
controlling a source of electromagnetic radiation to emit a wavelength modulated beam;
detecting the modulated beam or beams after transmission through a test medium;
processing the detected beam or beams to obtain a signal indicative of the absorption effects of one or more measurands,
wherein the processing includes correlating or convolving the indicative signal with a kernel function that is selective for a predicted signal feature.

Embodiment 2

A method according to embodiment 1, wherein the kernel function is a frequency-selective variable gain function that is adapted to suppress a predicted distortion of the indicative signal.

Embodiment 3

A method according to embodiment 1 or embodiment 2, wherein the kernel function is a frequency-selective variable gain function that is adapted to enhance a predicted absorption signal feature.

Embodiment 4

A method according to embodiment 3, wherein the kernel function is adapted to transform the frequency spectrum of the predicted absorption signal feature to a higher or lower frequency to isolate the predicted absorption signal feature from frequency-specific distortions of the indicative signal.

Embodiment 5

A method according to embodiment 1, wherein the kernel function is selected to have a profile related to a predicted distortion of the baseline signal.

Embodiment 6

A method according to embodiment 5, wherein the kernel function is selected to have a profile related to predicted sinusoidal or pseudo-sinusoidal fluctuations of the baseline signal.

Embodiment 7

A method according to any one of the preceding embodiments, wherein the processing includes correlating or convolving the indicative signal with a first kernel function that is selective for predicted distortions of the baseline signal, applying a first correction to the indicative signal to reduce the predicted signal distortions, and then correlating or convolving the corrected indicative signal with a second kernel function that is selective for a predicted absorption signal feature.

Embodiment 8

A method according to any one of the preceding embodiments, wherein a kernel function is selected to enhance a component of the indicative signal corresponding to a predicted absorption signal characteristic, thereby to reduce the relative effect of baseline signal fluctuations on absorption measurement.

Embodiment 9

A method according to embodiment 5 or embodiment 6, wherein a kernel function that is selective for a predicted baseline distortion from optical interference, is correlated or convolved with the indicative signal to determine the optical interference effects on the baseline, and a corrected baseline with reduced baseline distortion is generated by subtracting the determined optical interference effects from the indicative signal.

Embodiment 10

A method according to embodiment 5 or embodiment 6, wherein an inverse kernel corresponding to the inverse of the baseline distortion is correlated or convolved with the indicative signal to determine the inverse of the baseline distortion, and a corrected baseline is generated by adding the determined inverse baseline distortion to the indicative signal.

Embodiment 11

A method according to any preceding embodiment, wherein the kernel function or functions used in the correlation or convolution have profiles selected from the group comprising: Lorentzian, Gaussian, Voigt, sinusoidal or a combination of these profiles.

Embodiment 12

A method according to any preceding embodiment, wherein the kernel used in the correlation or convolution is derived from an empirical shape, a theoretical shape or a combination of both.

Embodiment 13

A method according to any preceding embodiment, wherein the indicative signal is derived by harmonic wavelength modulation absorption spectroscopy detection, and the method comprises measurement of a detected reference signal to compensate for intensity fluctuations and correlation or convolution with a kernel function to reduce distortions of the reference signal.

Embodiment 14

A method according to embodiment 13, wherein the reference signal is a modulation burst signal measured using harmonic wavelength modulation absorption spectroscopy, and wherein a kernel function to be correlated or convolved with the indicative signal is a kernel function selected to enhance signal features due the harmonic modulation burst and reduce the effect of signal features due to the effects of optical interference on the baseline, thereby to reduce the relative effect of optical interference on the baseline of the modulation burst signal.

Embodiment 15

A method according to embodiment 14, wherein a kernel is correlated or convolved with the indicative signal to enhance signal features due to the harmonic modulation burst and absorption and to reduce the effects of optical interference on the baseline, thereby to reduce the relative effect of optical interference on the baseline.

Embodiment 16

A method according to any preceding embodiment, wherein a correlation or convolution is carried out in the frequency domain.

Embodiment 17

A method according to embodiment 16, wherein a correlation or convolution is carried out using fast Fourier transforms and inverse transforms.

Embodiment 18

A method according to any one of embodiments 1 to 15, wherein a correlation or convolution is carried out in the time domain.

Embodiment 19

The method of any preceding embodiment, wherein the source of electromagnetic radiation is a tunable diode laser and the laser's bias current is ramped up and down across a range of values to vary the laser's output beam across a range of wavelengths; and wherein the method further comprises identifying absorption wavelengths of gases in a sample gas and choosing the location of at least one modulation burst reference signal within the wavelength range to avoid the identified absorption wavelengths.

Embodiment 20

The method of any preceding embodiment, wherein the processing further includes determining the concentration of one or more measurand species.

Embodiment 21

The method of any preceding embodiment, wherein the test medium is a gas from an artificial or natural process.

Embodiment 22

The method of any preceding embodiment, wherein the source of elecromagnetic radiation is a diode laser controlled by a continuous and variable drive current.

Embodiment 23

A method according to any one of the preceding embodiments, wherein the method comprises measurement of a modulation burst reference signal to compensate for intensity fluctuations, wherein the burst signal modulation is one of:
  amplitude modulation at fixed phase;
  phase modulation at fixed amplitude; or
  a combination of phase modulation and amplitude modulation.

Embodiment 24

A method according to any one of the preceding embodiments, wherein the test medium is a sample gas produced in a chamber associated with an artificial or natural process, and wherein the source of electromagnetic radiation is positioned such that it emits the photon beam through at least a portion of said chamber.

Embodiment 25

A method according to any one of embodiments 1 to 23, wherein the test medium is a sample gas flowing through an extractive system, and wherein the source of electromagnetic radiation is positioned such that it emits the photon beam through at least a portion of said extractive system.

Embodiment 26

An absorption spectroscopy system, comprising:
  a source of electromagnetic radiation for emitting a wavelength modulated photon beam;
  a detector for detecting the modulated photon beam or beams after transmission through a test medium;
  a signal processing unit for processing the detected beam or beams to obtain a signal indicative of the absorption effects of one or more measurands, wherein the processing unit is adapted to perform processing including correlating or convolving the indicative signal with a kernel function that is selective of a predicted signal feature, for reducing the effect of signal distortions on a measurement of absorption effects of the one or more measurands.

Embodiment 27

An absorption spectroscopy system according to embodiment 26, comprising one or more sources or electromagnetic radiation and one or more detectors, and one or more signal processing units adapted to perform a method according to any one of claims 1 to 25.

Embodiment 28

An absorption spectroscopy system according to embodiment 26 or embodiment 27 including an internal reference cell for measuring absorption characteristics under controlled or known conditions.

Embodiment 29

An absorption spectroscopy system according to embodiment 28, including a processing unit for processing a reference signal obtained using the internal reference cell by convolving or correlating with a kernel function that is selective for a predicted signal feature.

Embodiment 30

An absorption spectroscopy system according to embodiment 28, including a processing unit adapted to generate a kernel function related to an absorption profile obtained using the internal reference cell, which kernel function is convolved or correlated with the indicative signal obtained by transmission of the modulated beam through the test medium.

What is claimed is:

1. A method for reducing the effects of distortions on the baseline of an absorption signal within an absorption spectroscopy system, comprising the steps of:
controlling a source of electromagnetic radiation to emit a wavelength modulated beam;
using a detector to detect the modulated beam or beams after transmission through a test medium; and
using a signal processor to process the detected beam or beams to obtain a signal indicative of the absorption effects of one or more measurands,
wherein the processing includes correlating or convolving the indicative signal with a kernel function that is selective for a predicted signal distortion effect arising from at least one of optical interference or electromagnetic interference, wherein the kernel function is a frequency-selective variable gain function that is adapted to either suppress or enhance a predicted signal distortion effect, and wherein correlating or convolving the indicative signal with the kernel function reduces the effect of baseline signal distortions on a measurement of absorption effects of the one or more measurands.

2. A method according to claim 1, wherein the kernel function is adapted to transform the frequency spectrum of the predicted absorption signal distortion effect to a higher or lower frequency to isolate the predicted distortion effect from frequency-specific distortions of the indicative signal.

3. A method according to claim 1, wherein the kernel function is selected to have a profile related to a predicted distortion of the baseline signal.

4. A method according to claim 3, wherein the kernel function is selected to have a profile related to predicted sinusoidal or pseudo-sinusoidal fluctuations of the baseline signal.

5. A method according to claim 1, wherein the processing includes correlating or convolving the indicative signal with a first kernel function that is selective for predicted distortions of the baseline signal, applying a first correction to the indicative signal to reduce the predicted signal distortions, and then correlating or convolving the corrected indicative signal with a second kernel function that is selective for a predicted absorption signal feature.

6. A method according to claim 1, wherein a kernel function is selected to enhance a component of the indicative signal corresponding to a predicted absorption signal characteristic, thereby to reduce the relative effect of baseline signal fluctuations on absorption measurement.

7. A method according to claim 3, wherein a kernel function, that is selective for a predicted baseline distortion resulting from optical interference, is correlated or convolved with the indicative signal to determine the optical interference effects on the baseline, and a corrected baseline with reduced baseline distortion is generated by subtracting the determined optical interference effects from the indicative signal.

8. A method according to claim 3, wherein an inverse kernel, corresponding to the inverse of the baseline distortion, is correlated or convolved with the indicative signal to determine the inverse of the baseline distortion, and a corrected baseline is generated by adding the determined inverse baseline distortion to the indicative signal.

9. A method according to claim 1, wherein the kernel function or functions used in the correlation or convolution have profiles selected from the group comprising: Lorentzian, Gaussian, Voigt, sinusoidal or a combination of these profiles.

10. A method according to claim 1, wherein the kernel used in the correlation or convolution is derived from an empirical shape, a theoretical shape or a combination of both.

11. A method according to claim 1, wherein the indicative signal is derived by harmonic wavelength modulation absorption spectroscopy detection, and the method comprises measurement of a detected reference signal to compensate for intensity fluctuations and correlation or convolution with a kernel function to reduce distortions of the reference signal.

12. A method according to claim 11, wherein the reference signal is a modulation burst signal measured using harmonic wavelength modulation absorption spectroscopy, and wherein a kernel function to be correlated or convolved with the indicative signal is a kernel function selected to enhance signal features due the harmonic modulation burst and reduce the effects of optical interference on the baseline, thereby to reduce the relative effect of optical interference on the baseline of the modulation burst signal.

13. A method according to claim 12, wherein a kernel is correlated or convolved with the indicative signal to enhance signal features due to the harmonic modulation burst and absorption and to reduce the effects of optical interference on the baseline, thereby to reduce the relative effect of optical interference on the baseline.

14. A method according to claim 1, wherein a correlation or convolution is carried out in the frequency domain.

15. A method according to claim 14, wherein a correlation or convolution is carried out using fast Fourier transforms and inverse transforms.

16. A method according to claim 1, wherein a correlation or convolution is carried out in the time domain.

17. The method of claim 1, wherein the source of electromagnetic radiation is a tunable diode laser and the laser's bias current is ramped up and down across a range of values to vary the laser's output beam across a range of wavelengths; and wherein the method further comprises identifying absorption wavelengths of gases in a sample gas and choosing the location of at least one modulation burst reference signal within the wavelength range to avoid the identified absorption wavelengths.

18. The method of claim 1, wherein the processing further includes determining the concentration of one or more measurand species.

19. The method of claim 1, wherein the test medium is a gas from an artificial or natural process.

20. The method of claim 1, wherein the source of electromagnetic radiation is a diode laser controlled by a continuous and variable drive current.

21. A method according to claim 1, wherein the method comprises measurement of a modulation burst reference signal to compensate for intensity fluctuations, wherein the burst signal modulation is one of:
amplitude modulation at fixed phase;
phase modulation at fixed amplitude; or
a combination of phase modulation and amplitude modulation.

22. A method according to claim 1, wherein the test medium is a sample gas produced in a chamber associated with an artificial or natural process, and wherein the source of electromagnetic radiation is positioned such that it emits the photon beam through at least a portion of said chamber.

23. A method according to claim 1, wherein the test medium is a sample gas flowing through an extractive system, and wherein the source of electromagnetic radiation is positioned such that it emits the photon beam through at least a portion of said extractive system.

24. An absorption spectroscopy system, comprising:
a source of electromagnetic radiation for emitting a wavelength modulated photon beam;
a detector for detecting the modulated photon beam or beams after transmission through a test medium; and
a signal processor for processing the detected beam or beams to obtain a signal indicative of the absorption effects of one or more measurands, wherein the processing includes correlating or convolving the indicative signal with a kernel function that is selective for a predicted signal distortion effect arising from at least one of optical interference or electromagnetic interference, wherein the kernel function is a frequency-selective variable gain function that is adapted to either suppress or enhance a predicted signal distortion effect, and wherein correlating or convolving the indicative signal with the kernel function reduces the effect of baseline signal distortions on a measurement of absorption effects of the one or more measurands.

25. An absorption spectroscopy system according to claim 24, comprising one or more sources of electromagnetic radiation and one or more detectors, and one or more signal processing units.

26. An absorption spectroscopy system according to claim 24, including an internal reference cell for measuring absorption characteristics under controlled or known conditions.

27. An absorption spectroscopy system according to claim 26, including a processing unit for processing a reference signal obtained using the internal reference cell by convolving or correlating with a kernel function that is selective for a predicted signal distortion effect.

28. An absorption spectroscopy system according to claim 26, including a processing unit adapted to generate a kernel function related to an absorption profile obtained using the internal reference cell, which kernel function is convolved or correlated with the indicative signal obtained by transmission of the modulated beam through the test medium.

29. A method for reducing the effects of distortions on the baseline of an absorption signal within an absorption spectroscopy system, comprising the steps of:
controlling a source of electromagnetic radiation to emit a wavelength modulated beam;
using a detector to detect the modulated beam or beams after transmission through a test medium; and
using a signal processor to process the detected beam or beams to obtain a signal indicative of the absorption effects of one or more measurands,
wherein the processing includes correlating or convolving the indicative signal with a kernel function that is selective for a predicted sinusoidal or pseudo-sinusoidal signal distortion effect from optical interference, wherein the kernel function is a frequency-selective variable gain function that is adapted to either suppress or enhance a predicted signal distortion effect, and wherein correlating or convolving the indicative signal with the kernel function reduces the effect of baseline signal distortions on a measurement of absorption effects of the one or more measurands.

30. A method for reducing the effects of distortions on the baseline of an absorption signal within an absorption spectroscopy system, comprising the steps of:
controlling a source of electromagnetic radiation to emit a wavelength modulated beam;
using a detector to detect the modulated beam or beams after transmission through a test medium; and
using a signal processor to process the detected beam or beams to obtain a signal indicative of the absorption effects of one or more measurands,
wherein the processing includes correlating or convolving the indicative signal with a kernel function that is selective for a predicted signal distortion effect, and wherein the correlating or convolving the indicative signal with the kernel function reduces the effect of baseline signal distortions on a measurement of absorption effects of the one or more measurands,
wherein the indicative signal is derived by harmonic wavelength modulation absorption spectroscopy detection, and the method comprises measurement of a detected reference signal to compensate for intensity fluctuations and correlation or convolution with a kernel function to reduce distortions of the reference signal,
wherein the reference signal is a modulation burst signal measured using harmonic wavelength modulation absorption spectroscopy, and wherein a kernel function to be correlated or convolved with the indicative signal is a kernel function selected to enhance signal features due the harmonic modulation burst and reduce the effect of signal features due to the effects of optical interference on the baseline, thereby to reduce the relative effect of optical interference on the baseline of the modulation burst signal.

* * * * *